US008883517B2

(12) United States Patent
Cook

(10) Patent No.: US 8,883,517 B2
(45) Date of Patent: Nov. 11, 2014

(54) DETECTION OF ANTIBODIES

(75) Inventor: Neil James Cook, Lower Hutt (NZ)

(73) Assignee: Gemini Research Limited, Lower Hutt (NZ)

( * ) Notice: Subject to any disclaimer, the term of this patent is extended or adjusted under 35 U.S.C. 154(b) by 0 days.

(21) Appl. No.: 13/395,723

(22) PCT Filed: Sep. 14, 2010

(86) PCT No.: PCT/NZ2010/000183
§ 371 (c)(1),
(2), (4) Date: May 1, 2012

(87) PCT Pub. No.: WO2011/034445
PCT Pub. Date: Mar. 24, 2011

(65) Prior Publication Data
US 2012/0276655 A1 Nov. 1, 2012

(30) Foreign Application Priority Data

Sep. 15, 2009 (AU) ............................... 2009904459

(51) Int. Cl.
*G01N 33/559* (2006.01)
*G01N 33/564* (2006.01)
*G01N 33/561* (2006.01)

(52) U.S. Cl.
CPC ............ *G01N 33/564* (2013.01); *G01N 33/561* (2013.01)
USPC .............................. 436/515; 436/514; 422/69

(58) Field of Classification Search
CPC .................... A61K 2039/505; C07K 2319/00; G01N 2500/02; G01N 33/53; G01N 33/573; G01N 2800/24
USPC .................................................. 436/514, 515
See application file for complete search history.

(56) References Cited

U.S. PATENT DOCUMENTS

| | | | | |
|---|---|---|---|---|
| 5,518,881 | A | * | 5/1996 | Gordon et al. ............... 435/6.11 |
| 6,818,392 | B2 | | 11/2004 | Lou et al. |
| 7,531,639 | B2 | | 5/2009 | Lou et al. |
| 2009/0029388 | A1 | * | 1/2009 | Beeson .......................... 435/7.1 |

FOREIGN PATENT DOCUMENTS

| WO | WO 92/06105 | 4/1992 |
|---|---|---|
| WO | WO 00/17649 | 3/2000 |

OTHER PUBLICATIONS

Merryman et al., J. Clin Pathol 1991; 44:685-689.*
Written Opinion for International (PCT) Application No. PCT/NZ10/00183 mailed Jan. 10, 2011, 5 pages.
Supplementary European Search Report for European Patent Application No. 10817490.5 dated Jan. 22, 2013, 12 pages.
International Search Report for International (PCT) Patent Application No. PCT/NZ2010/000183, mailed Jan. 10, 2011, 3 pages.
Maeda "Assay of an Antitumor Protein, Neocarzinostatin, and Its Antibody by Fluorescence Polarization," Clinical Chemistry, 1978, vol. 24, No. 12, pp. 2139-2144.
Schultz et al. "Rapid Immunoassays Using Capillary Electrophoresis with Fluorescence Detection," Analytical Chemistry, 1993, vol. 65, No. 21, pp. 3161-3165.
Suzuki et al. "Immunoassay with Fluorescein-labelled Antigens—Device of a Method and Its Clinical Application," Japanese Journal of Experimental Medicine, 1979, vol. 49, No. 3, pp. 179-185.

* cited by examiner

*Primary Examiner* — Mark Shibuya
*Assistant Examiner* — Carmencita M Belei
(74) *Attorney, Agent, or Firm* — Aspire IP; Scott J. Hawranek

(57) ABSTRACT

The present invention relates to a method of detecting a target antibody, particularly a target autoantibody, in a sample, using a small molecule fluorophore-labelled target antigen, or a functional fragment, functional variant or functional derivative thereof that specifically binds to the target antibody. Detection is typically carried out using immunodiffusion or immunoelectrophoresis. The invention also relates to methods of diagnosing disease, particularly autoimmune disease, using small molecule fluorophore labelled target antigens and autoantigens. Small molecule fluorophore labelled target antigens, including autoantigens, are also disclosed, as are uses such.

9 Claims, 13 Drawing Sheets a)

a = 2.5mm
b = 3mm
c = 25mm
d = 37.5mm
e = 75mm b)

a = 2mm
b = 3mm
c = 6mm
d = 2mm
e = 37.5mm
f = 50mm
g = 45mm
h = 75mm

DETECTION OF ANTIBODIES

CROSS REFERENCE TO RELATED APPLICATIONS

This application is a national stage application under 35 U.S.C. 371 and claims the benefit of PCT Application No. PCT/NZ2010/000183 having an international filing date of Sep. 14, 2010, which designated the United States, which PCT application claimed the benefit of Australian Application No. 2009904459 filed Sep. 15, 2009, the disclosure of both the above-identified applications are incorporated herein by reference.

FIELD OF THE INVENTION

This invention relates to methods for detecting antibodies using small molecule fluorescently-labelled antigens, compositions containing small molecule fluorescently-labelled antigens and kits containing fluorescently labelled antigens for use in detecting antibodies.

BACKGROUND

Autoimmune Disorders

In normal healthy individuals, B lymphocytes which comprise part of the body's humoral immune system help provide protection against infection by producing antibodies. Antibodies are proteins that attack invasive microbes or other "foreign" substances, removing these substances from the body and thus combating infection. Some foreign substances are proteins that provoke an immune response; i.e., the production of antibodies, and are termed antigenic proteins, also referred to herein as protein antigens. Antibodies produced by the immune system can be highly specific in binding and removing the particular antigens which provoke their production. In those individuals with a normally functioning immune system, a wide variety of antibodies are built up over time. These antibodies target and recognize various antigens which challenge the body's immune system, identifying particular antigens as either threatening or non-threatening to the organism.

Normally, the immune system readily distinguishes two general categories; recognizing antigenic proteins as either "self" or "not self." "Self" antigens are typically recognized by the body's immune system as non-threatening, although this is not always the case. The body's immune system typically attacks only those antigens which are recognized as "not self."

Autoimmune disorders are diseases that result from the body's production of an inappropriate immune response directed against its own "self" antigens. Such responses are frequently tissue directed or tissue specific. For example, the immune system may cease to recognize one or more of the body's normal proteins as "self", creating antibodies termed autoantibodies, which target the body's own cells, tissues, and/or organs. The inflammation and damage caused by such attacks can lead to various autoimmune disorders.

The specific cause of autoimmune disease is unknown. Some evidence suggests that certain individuals have an inherited predisposition to develop autoimmune disease. Alternatively, some autoimmune disease, (e.g., rheumatic fever), appears to be triggered by bacterial or viral infection. The consequent immune response produces antibodies or T-cells which attack normal cells that display certain proteins that may structurally resemble (at least in part) the structure of certain proteins of the infecting microorganism(s).

Autoimmune disorders are categorized into two general types. Systemic autoimmune diseases are those diseases that cause damage to many organs. Localized, or tissue specific autoimmune diseases are those diseases which directly damage only a single organ or tissue. The distinctions between these two categories of disease, however, are not absolute. Frequently the deleterious effects of localized autoimmune disorders are not limited to the direct effects observed in a single organ or tissue, and may extend indirectly to other body organs and systems.

Common types of autoimmune disease include Rheumatoid arthritis (RA) and Juvenile RA (JRA) (joints; less commonly lung, skin), Type 1 Diabetes Mellitus (pancreas islets), Lupus [Systemic Lupus Erythematosus] (skin, joints, kidneys, heart, brain, red blood cells, other), Hashimoto's thyroiditis, Graves' disease (thyroid), Scleroderma (skin, intestine, less commonly lung), Celiac disease, Crohn's disease, Ulcerative colitis (GI tract), Sjogren's syndrome (salivary glands, tear glands, joints), Multiple sclerosis, Goodpasture's syndrome (lungs, kidneys), Addison's disease (adrenal), Wegener's granulomatosis (blood vessels, sinuses, lungs, kidneys), Primary biliary cirrhosis, Sclerosing cholangitis, Autoimmune hepatitis (liver), Polymyalgia Rheumatica (large muscle groups), Temporal Arteritis/Giant Cell Arteritis (arteries of the head and neck), and Guillain-Barre syndrome (nervous system).

Diagnosis of Autoimmune Disorder

The diagnosis of autoimmune disorders is generally carried out through a combination of clinical analysis of symptoms (presentation), blood tests to measure autoantibodies, inflammation and organ function, and other procedures including physical examination and/or X-rays.

Blood tests which measure autoantibodies are typically performed by detecting autoantibodies present in a serum sample taken from a subject having or suspected of having an autoimmune disorder. Commonly employed blood assays include Ouchterlony double immunodiffusion assays (DID) and counterimmunoelectrophoresis (CIE). These types of assays visualize precipitins (agglutinations) of autoantibody/antigen complexes formed by the binding of particular autoantibodies to their cognate antigens (Bunn & Kveder, 1993 *Man. Biol. Mark. Dis. A*3:1-12; Kluwer Academic). DID assays, for example, may be carried out in agar plates, with autoantigens placed in a central well symmetrically surrounded by peripheral wells. The peripheral wells are then loaded with test samples which contain antibodies that are diagnostic for a particular autoimmune disorder. The sample and test antigens are allowed to diffuse through the agarose, where agglutination of autoantibodies in the sample with a cognate autoantigen leads to the formation of an antibody/antigen complex. Extensive crosslinking of autoantibodies and autoantigens will occur in the agarose gel at a location where autoantibodies in the test sample and autoantigens from the peripheral wells reach equivalent concentrations due to diffusion. Such cross-linked complexes are termed precipitins. Precipitin formation is then visualized optically by direct light scattering of the autoantibody/test antigen complex.

Due to the specificity of binding of a given autoantibody for its cognate antigen, DID assays allow for positive detection of autoantibodies present in the sample being tested. Known DID assays, however, are non-quantitative and can suffer from a relative lack of sensitivity. In addition, relatively high numbers of autoantibodies in a sample are generally required for precipitin visualization. For these reasons, known DID assays may produce false negative results in some circumstances. Confirmation of a negative result returned from a DID assay, in view of clinical presentation of autoimmune disorder related symptoms requires additional tests be performed. This can result in additional expense, time lost before the initiation of any treatment regimen and general inconvenience to the subject.

Alternatively, autoantibodies present in a sample may be detected using a common biochemical technique called an enzyme-linked immunosorbent assay (ELISA), or enzyme immunoassay (EIA) (Charles P. J. et al. 1993 *Man. Biol. Mark. Dis. A*5:1-23; Kluwer Academic). In general terms, antibodies in a sample may be detected by ELISA as follows: An amount of a known antigen which binds specifically to a particular antibody is affixed to a surface, for example, the bottom of a microtitre plate well. A sample containing an unknown amount of the antibody to be detected is then placed into the well, allowing binding of the antigen to the antibody. The bound antibody is then detected using an anti-hIgG enzyme conjugate (anti-human immunoglobulin G).

Alternatively, a substrate for an enzyme bound to the antibody may be added to microtitre plate well, where activity of the enzyme converts this substrate to some type of detectable signal. The antibody may be covalently linked to an enzyme, or may be itself detected by use of an enzyme linked secondary antibody. Visualization of the detectable signal depends on the enzymatic substrate employed. Some ELISAs utilize chromogenic substrates, whereas other, more sensitive assays employ fluorogenic substrates. In the case of fluorescence ELISA, fluorescence detection of the antigen/antibody complexes allows the amount of antigen in the sample to be inferred by measuring the magnitude of the fluorescence.

An ELISA can also be used to detect autoantibodies in a blood sample obtained from a subject. Methods employing ELISA can detect very low concentrations of autoantibodies in a sample. However, ELISA methods of detection are prone to false positives due to the extreme sensitivity of the assay.

Consequently, there is a need for alternative methods of detecting autoantibodies in a sample suspected of containing autoantibodies that can provide a clinician with a more robust diagnostic tool available as a single test. A single test could provide the clinician greater confidence in his or her diagnosis without incurring the additional subject expense of further confirmatory testing, may be performed quickly and easily, and will also reduce the inconvenience to a subject of requiring further testing, potentially allowing an earlier initiation of the appropriate treatment regime.

It is an object of the present invention therefore, to at least go some way towards addressing the deficiencies of the prior art tests as outlined above by providing improved methods and/or compositions and/or kits that can be used to detect autoantibodies, and/or to at least provide the public with a useful choice.

SUMMARY OF THE INVENTION

In a first aspect, the present invention provides a small molecule fluorophore-labelled target antigen (SMFLTA) or functional fragment, functional variant or functional derivative thereof.

In one embodiment the small molecule fluorophore-labelled target antigen is a small molecule fluorophore-labelled target autoantigen (SMFLTAA) or functional fragment, functional variant or functional derivative of an SMFLTAA.

Preferably the SMFLTAA, functional fragment, functional variant or functional derivative thereof is, or is derived from a nuclear autoantigen.

Preferably nuclear autoantigen selected from the group consisting of Jo-1 antigen, (Ro60) SSA antigen, (La) SSB antigen, Sm antigen, Sm/RNP complex antigen, Scl-70 antigen or a functional fragment, functional variant, or functional derivative thereof.

Preferably the SMFLTAA, or functional fragment, functional variant or functional derivative thereof is, or is derived from an autoantigen that is specifically associated with a particular autoimmune disorder or disease.

In one embodiment the autoimmune disorder is selected from the group consisting of mixed connective tissue disease, systemic lupus erythematosus (SLE), Sjogren's syndrome, scleroderma, polymyositis, systemic sclerosis, dermatomyositis, rheumatoid arthritis and neonatal lupus syndrome.

In one embodiment the SMFLTA or SMFLTAA is a fluorescently labelled target antigen or target autoantigen isolated from a mammal. Preferably the mammal is a human, monkey, cow, sheep, pig, rat, or mouse. Preferably the mammal is a human a sheep or a cow. More preferably the mammal is a cow.

In one embodiment the SMFLTA or SMFLTAA is prepared from a target antigen, target autoantigen or functional fragment, functional variant or functional derivative thereof that has been isolated from a first species of mammal, whereas the target antibody or target autoantibody that is specifically bound by the SMFLTA or SMFLTAA of the invention is present in a sample obtained from a different species of mammal.

Preferably the SMFLTA or SMFLTAA is prepared from a target antigen, target autoantigen or functional fragment, functional variant or functional derivative thereof that has been isolated from a cow or a sheep. More preferably the target antigen, target autoantigen or functional fragment, functional variant or functional derivative thereof has been prepared from a cow. Preferably the prepared SMFLTA or SMFLTAA is used to detect a target antibody or target autoantibody present in a sample obtained from a human.

In one embodiment the SMFLTA or SMFLTAA is prepared from a target antigen, target autoantigen or functional fragment, functional variant or functional derivative thereof that has been recombinantly expressed from a polynucleotide sequence encoding the target antigen, target autoantigen or functional fragment, functional variant or functional derivative thereof. Preferably the polynucleotide sequence is comprised in an expression vector.

In another aspect, the invention provides a composition comprising a SMFLTA or SMFLTAA, functional fragment, functional variant or functional derivative thereof according to the invention and a carrier or diluent.

In another aspect the invention provides kits comprising
a) a SMFLTA, functional fragment, functional variant or functional derivative thereof according to the invention;
b) an immunoassay device configured to allow the SMFLTA, functional fragment, functional variant or functional derivative thereof, of the invention to contact a sample under conditions which allow the SMFLTA to bind to a target antibody,
c) instructions for detecting the SMFLTA, functional fragment, functional variant or functional derivative thereof, bound to the target antibody.

Preferably the instructions direct the fluorescence detection of the SMFLTA, functional fragment, functional variant or functional derivative thereof.

Preferably the immunoassay device is an immunoprecipitation device.

Preferably contacting the target antibody with the SMFLTA, functional fragment, functional variant or functional derivative thereof is carried out under conditions that allow immunoprecipitation of the SMFLTA, functional fragment, functional variant or functional derivative thereof with its target antibody.

In one embodiment the SMFLTA is an SMFLTAA, or functional fragment, functional variant or functional derivative thereof.

Preferably the SMFLTAA, functional fragment, functional variant or functional derivative thereof is, or is derived from a nuclear autoantigen selected from the group consisting of Jo-1 antigen, (Ro) SSA antigen, (La) SSB antigen, Sm antigen, Sm/RNP complex antigen, Scl-70 antigen or a functional fragment, functional variant or functional derivative thereof.

Preferably the SMFLTAA, functional fragment, functional variant or functional derivative thereof is, or is derived from an autoantigen that is specifically associated with a particular autoimmune disorder or disease.

In one embodiment the autoimmune disorder is selected from the group consisting of mixed connective tissue disease, systemic lupus erythematosus (SLE), Sjogren's syndrome, scleroderma, polymyositis, systemic sclerosis, dermatomyositis, rheumatoid arthritis and neonatal lupus syndrome.

Preferably the kit comprises a carrier or diluent for the SMFLTA or SMFLTAA or a functional fragment, functional variant or functional derivative thereof. The SMFLTA or SMFLTAA or a functional fragment, functional variant or functional derivative thereof may be dissolved in the carrier or diluent or the carrier or diluent may be present separately for later preparation of an SMFLTA or SMFLTAA composition. Preferably the separate SMFLTA or SMFLTAA or a functional fragment, functional variant or functional derivative thereof is lyophilized.

In one embodiment the kit is for use in a method of detecting a target antibody or target autoantigen comprising contacting a blood-derived sample obtained from a subject who has or is suspected of having an autoimmune disease or disorder with an SMFLTA or SMFLTAA according to the invention and detecting the presence of the SMFLTA or SMFLTAA bound to the target antibody or target autoantibody by fluorescence detection.

Preferably the blood-derived sample is a serum or plasma sample.

In one embodiment the subject displays a clinical phenotype which is indicative or suggestive of a particular autoimmune disorder as described herein.

In one embodiment the kit is for use in a method of the invention by screening of clinical samples obtained from subjects as described herein, wherein the method is performed concurrently with suitable controls either lacking target autoantibodies or containing known concentrations of control autoantibodies.

In one embodiment the contacting of the sample with the SMFLTA, SMFLTAA, or functional fragment, functional variant or functional derivative thereof is carried by double immunodiffusion (DID) assay or counter-immunoelectrophoresis (CIE) assay.

In one embodiment, the contacting is carried out using an immunoprecipitation device. Preferably the immunoprecipitation device is a micro-immunodiffusion device.

In another embodiment the immunoprecipitation device is a counterimmunoelectrophoresis device. Preferably the counterimmunoelectrophoresis device is a micro-counterimmunoelectrophoresis device.

Preferably the DID assay is an asymmetric DID (ADID) assay. Preferably the CIE assay is a micro-CIE assay.

In another aspect the invention provides a method of detecting a target antibody in a sample, the method comprising:

a) contacting the sample with a SMFLTA or a functional fragment, functional variant or functional derivative of an SMFLTA that specifically binds to a target antibody, and b) detecting the presence of the target antibody bound to the SMFLTA or functional fragment, functional variant or functional derivative thereof by fluorescence detection.

Preferably the contacting in a) is carried out under conditions that allow immunoprecipitation of the SMFLTA, functional fragment, functional variant or functional derivative thereof, with the target antibody.

Preferably the detecting in b) is fluorescence detection of the SMFLTA, functional fragment, functional variant or functional derivative thereof in the immunoprecipitate.

In one embodiment the SMFLTA is a SMFLTAA or functional fragment, functional variant or functional derivative of an SMFLTAA. The method is especially useful for detecting autoantibodies.

Preferably the SMFLTAA functional fragment, functional variant or functional derivative thereof is, or is derived from, a nuclear autoantigen selected from the group consisting of Jo-1 antigen, (Ro60) SSA antigen, (La) SSB antigen, Sm antigen, Sm/RNP complex antigen, Scl-70 antigen or a functional fragment, functional variant or functional derivative thereof.

Preferably the SMFLTAA functional fragment, functional variant or functional derivative thereof is, or is derived from an autoantigen that is specifically associated with a particular autoimmune disorder or disease.

In one embodiment the autoimmune disorder is selected from the group consisting of mixed connective tissue disease, systemic lupus erythematosus (SLE), Sjogren's syndrome, scleroderma, polymyositis, systemic sclerosis, dermatomyositosis, rheumatoid arthritis and neonatal lupus syndrome.

In one embodiment the sample is a blood-derived sample obtained from a subject who has or is suspected of having an autoimmune disorder or disease.

Preferably the blood-derived sample is a serum sample.

Preferably the sample is a clinical sample obtained from a subject having or suspected of having a particular autoimmune disorder wherein the method is performed concurrently with suitable controls either lacking target antibodies or containing known concentrations of control antibodies.

In one embodiment the subject who has or is suspected of having an autoimmune disorder or disease is a subject displaying a clinical phenotype which is indicative or suggestive of a particular autoimmune disorder as described herein.

In one embodiment the contacting of the sample with the SMFLTA, SMFLTAA or functional fragment, functional variant or functional derivative thereof is carried out by double immunodiffusion (DID) assay or counter-immunoelectrophoresis (CIE) assay. Preferably the contacting is performed using an immunoprecipitation device.

In one embodiment the immunoprecipitation device is an immunodiffusion device. More preferably the immunoprecipitation device is a micro-immunodiffusion device.

In another embodiment the immunoprecipitation device is a counterimmunoelectrophoresis device. Preferably the counterimmunoelectrophoresis device is a micro-counterimmunoelectrophoresis device.

Preferably the DID assay is an asymmetric DID (ADID) assay. Preferably the CIE assay is a micro-CIE assay.

In another aspect the invention provides a method of diagnosing an autoimmune disease or disorder in a subject by detecting a target autoantibody in a sample obtained from the subject, the method comprising;

a) contacting the sample with an SMFLTAA or functional fragment, functional variant or functional derivative thereof that specifically binds a target autoantibody, and b) detecting the presence of the target autoantibody bound to the SMFLTAA or functional fragment, functional variant or functional derivative thereof by fluorescence detection.

Preferably the contacting in a) is carried out under conditions that allow immunoprecipitation of the SMFLTAA, functional fragment, functional variant or functional derivative thereof, with the target autoantibody.

Preferably the detecting in b) is fluorescence detection of the SMFLTAA, functional fragment, functional variant or functional derivative thereof in the immunoprecipitate.

In another aspect the invention provides the use of a composition or kit according to the invention for diagnosing an autoimmune disease or disorder in a subject, the method comprising;

a) contacting a sample obtained from the subject with an SMFLTAA or a functional fragment, functional variant or functional derivative of an SMFLTAA that specifically binds to a target autoantibody, and b) detecting the presence of the target autoantibody bound to the SMFLTAA or functional fragment, functional variant or functional derivative thereof by fluorescence detection.

Preferably the contacting in a) is carried out finder conditions that allow immunoprecipitation of the SMFLTAA, functional fragment, functional variant or functional derivative thereof, with the target antibody.

Preferably the detecting in b) is fluorescence detection of the SMFLTAA, functional fragment, functional variant or functional derivative thereof in the immunoprecipitate.

In one embodiment, the invention provides the use of a composition or kit according to the invention for diagnosing an autoimmune disease or disorder in a subject, the method comprising;

a) contacting the sample with a SMFLTAA, functional fragment, functional variant or functional derivative thereof, that specifically binds a target autoantibody under conditions that allow immunoprecipitation of the SMFLTAA, functional fragment, functional variant or functional derivative thereof, with the target autoantibody, and b) detecting the presence of the precipitated target autoantibody in the immunoprecipitate by fluorescence detection of the SMFLTAA, functional fragment, functional variant or functional derivative thereof, in the immunoprecipitate.

In one embodiment the SMFLTAA, functional fragment, functional variant or functional derivative thereof is, or is derived from a nuclear autoantigen selected from the group consisting of Jo-1 antigen, (Ro60) SSA antigen, (La) SSB antigen, Sm antigen, Sm/RNP complex antigen, Scl-70 antigen, or functional fragment, functional variant or functional derivative thereof.

Preferably the SMFLTAA, functional fragment, functional variant or functional derivative thereof is, or is derived from an autoantigen that is specifically associated with a particular autoimmune disorder or disease.

In one embodiment the autoimmune disorder is selected from the group consisting of mixed connective tissue disease, systemic lupus erythematosus (SLE), Sjogren's syndrome, scleroderma, polymyositis, systemic sclerosis, dermatomyositosis, rheumatoid arthritis and neonatal lupus syndrome.

In one embodiment the conditions that allow immunoprecipitation of the SMFLTAA, functional fragment, functional variant or functional derivative thereof with the target autoantibody are sufficient to allow diffusion of the target autoantibody and the SMFLTAA, functional fragment, functional variant or functional derivative thereof through a gel, preferably an agarose gel, to reach equivalent concentrations at a particular location where the immunoprecipitate is formed.

Preferably the agarose gel is about 0.3% to about 1.5% agarose, more preferably the agarose gel is about 0.5% to 1.2% agarose. Most preferably the agarose gel is 0.8% to 1.0% agarose.

In one embodiment the target antibody or target autoantibody is detected according to a method of the invention in a blood-derived sample obtained from a subject at a dilution of from about 1:1 to about 1:256 (serum:diluent).

Preferably the blood derived sample is a serum sample. More preferably the dilution is from about 1:8 to about 1:128, or, is from about 1:16 to about 1:128, or is from about 1:32 to about 1:128, or is from about 1:64 to about 1:128. Most preferably the dilution is about 1:128.

BRIEF DESCRIPTION OF THE DRAWINGS

Preferred embodiments of invention will now be described with reference to the figures in, the accompanying drawings by way of example only. It is to be understood that the invention is not limited thereto. Throughout the remainder of the description SSA as used herein refers to purified (Ro60) SSA antigen.

Comparison of labelled and unlabelled SSA antigen visualized as follows; A) after SDS electrophoresis by Coomassie-blue staining; B) after SDS electrophoresis by blue light-transillumination with amber filter; C) after SDS electrophoresis and electrotransfer by immunoblotting using human autoantibodies specific for SSA.

Figure 2:
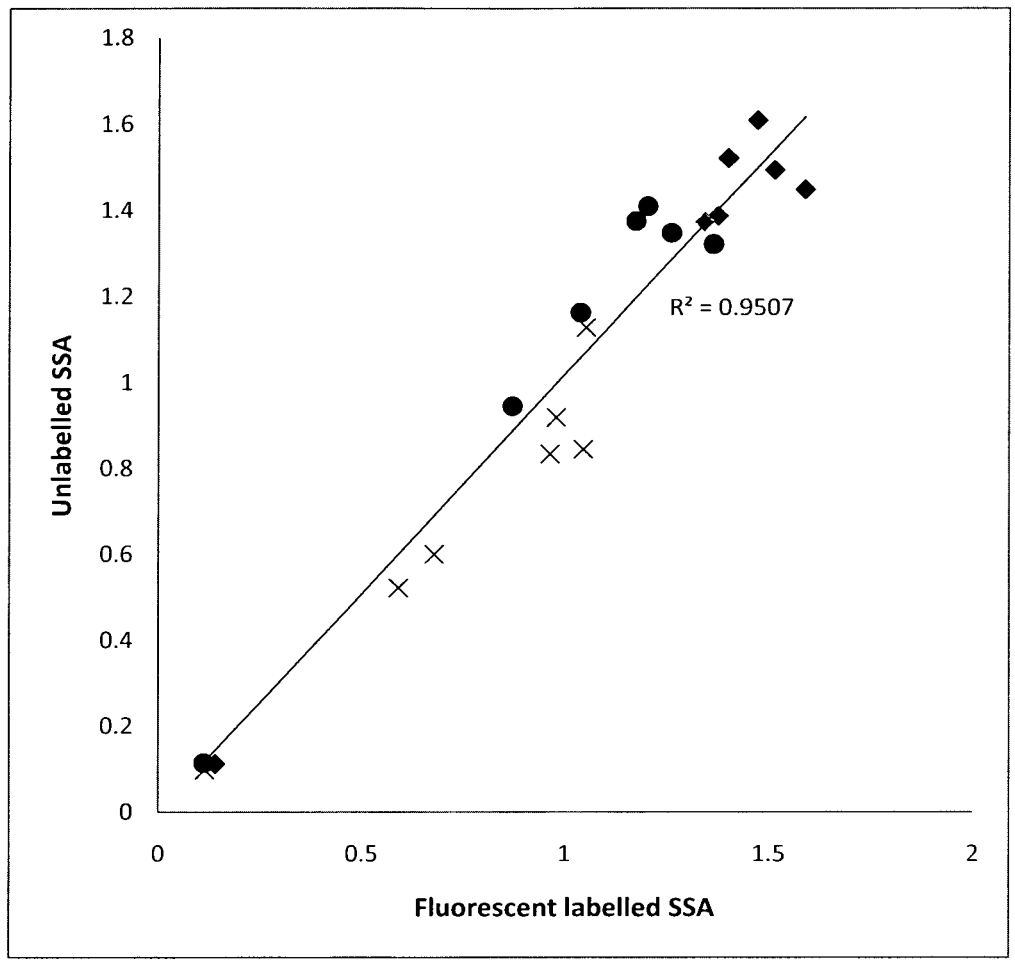

FIG. 2: Binding of labelled vs. unlabelled SSA antigen as assessed by ELISA

A graph showing the binding ability of small molecule fluorescence-labelled (AlexaFluor 488) and unlabelled SSA antigen to bind the subject autoantibodies as determined by ELISA. Antigen coating concentration: ♦=1.0 ug/ml; ●=0.5 ug/ml; x=0.25 ug/ml.

Figure 3:
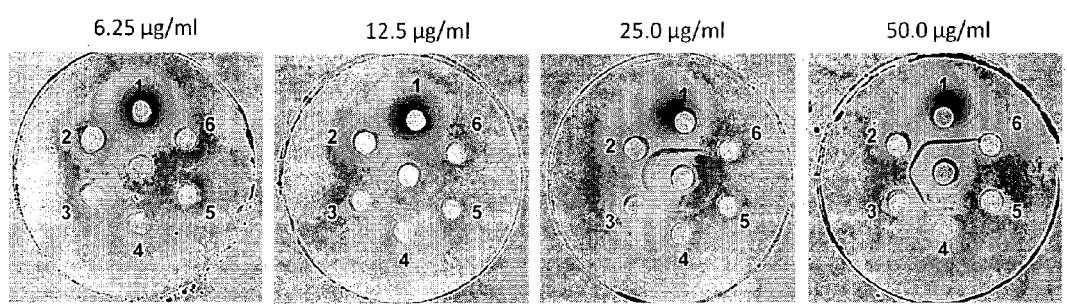

FIG. 3: Detection of anti-SSA antibodies by double immunodiffusion (DID).

Fluorescence visualization of anti-SSA antibodies in serum obtained from a subject (wells 1-6) by double immunodiffusion assay. The concentration of serum decreases from wells 1 to 6. The concentration of small molecule fluorescence-labelled SSA used to detect the anti-SSA antibodies (central well) increases from left to right.

Figure 4:
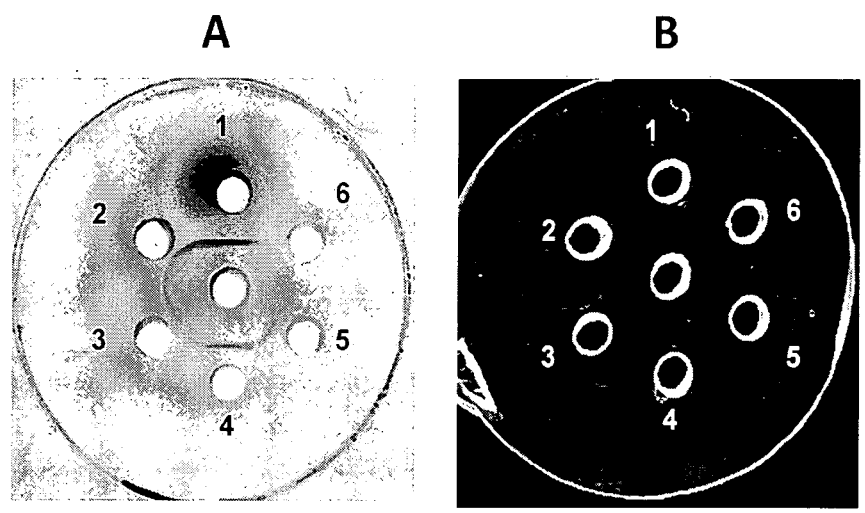

FIG. 4: Comparison of anti-SSA detection methods using double immunodiffusion

Anti-SSA in serum obtained from a subject is detected using small molecule fluorescence-labelled SSA and visualized by fluorescence detection or white light epi-illumination against a black background. A) blue light trans-illumination with amber filter; B) white light epi-illumination against a black background.

Figure 5:
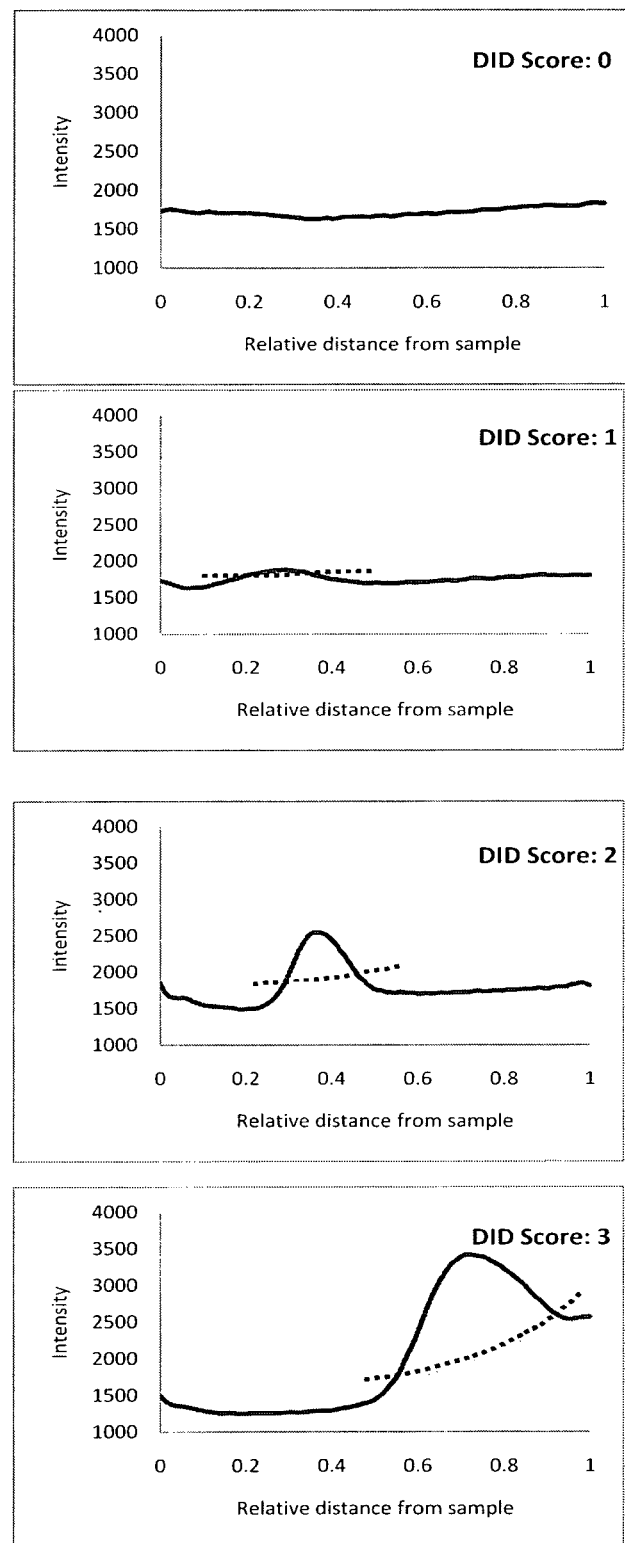

FIG. 5: Semi-quantitative evaluation of fluorescent double immunodiffusion

Densitometric image-scanning of the precipitin band formed by anti-SSA/small molecule fluorescence-labelled SSA binding.

Figure 6:
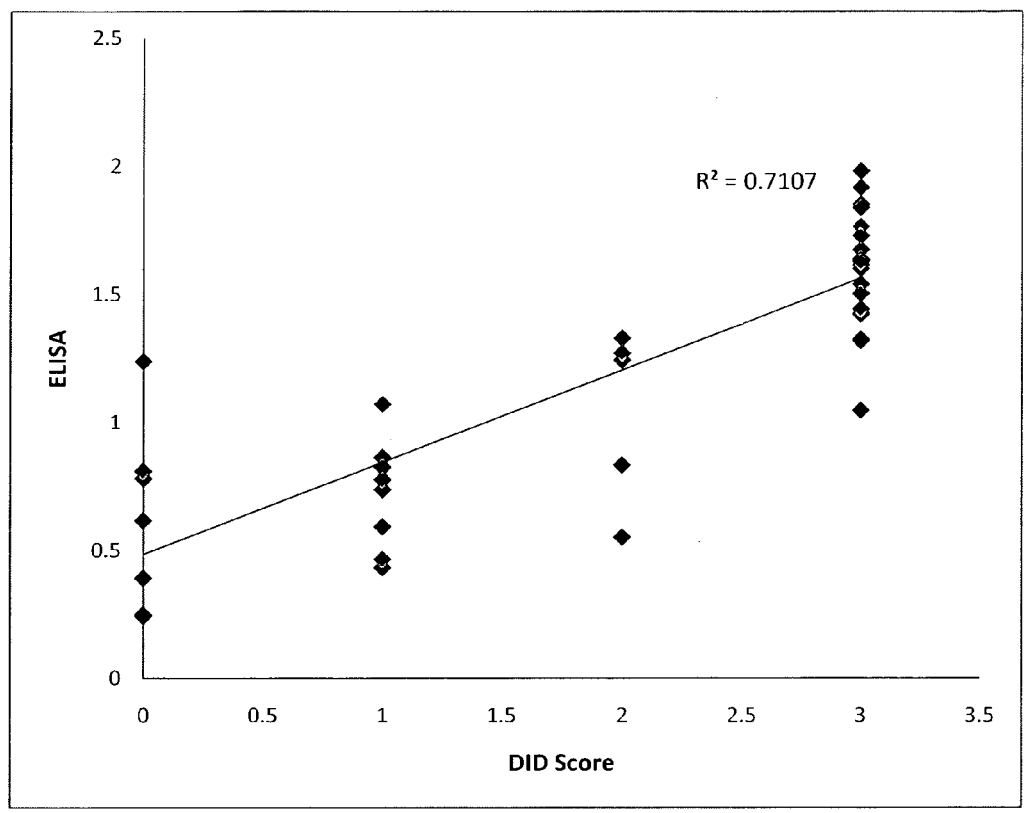

FIG. 6: Detection of anti-SSA antibodies: comparison of double immunodiffusion and ELISA A graphical depiction of anti-SSA/small molecule fluorescence-labelled SSA binding determined by direct ELISA and by double immunodiffusion. Plotting of the double immunodiffusion score and ELISA absorbance illustrates a good correlation ($r^2=0.7107$) between the two methods of SSA autoantibody measurement.

Figure 7:
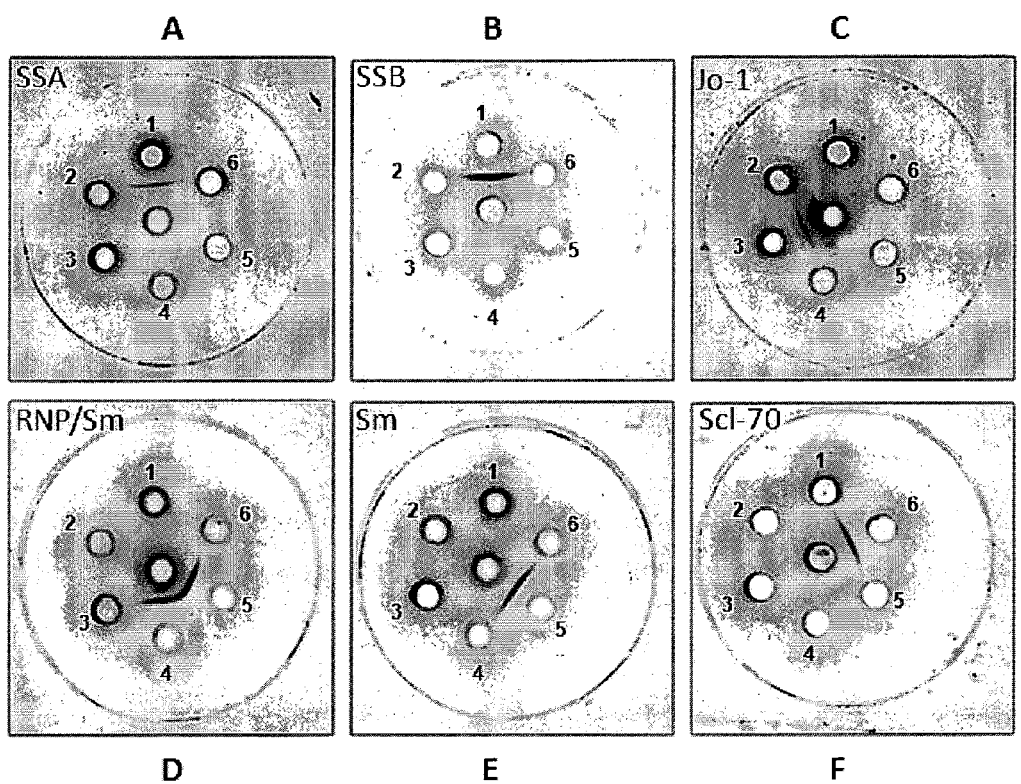

FIG. 7: Detection specificity of different anti-extractable nuclear autoantigens (ENA)

Double immunodiffusion assays of the invention showing fluorescence detection of six different autoantibodies in serum samples obtained from a subject using small molecule fluorescence-labelled autoantigens according to the invention. Autoantibodies: well 1, anti-SSA and anti-SSB; well 2, healthy donor (no autoantibodies); well 3, anti-Jo-1; well 4, anti-RNP/Sm; well 5, anti-Sm; well 6, anti-Scl-70. Small molecule fluorescence-labelled autoantigens: A) SSA; B) SSB; C) Jo-1; D) RNP/Sm; E) Sm, and F) Scl-70.

Figure 8:
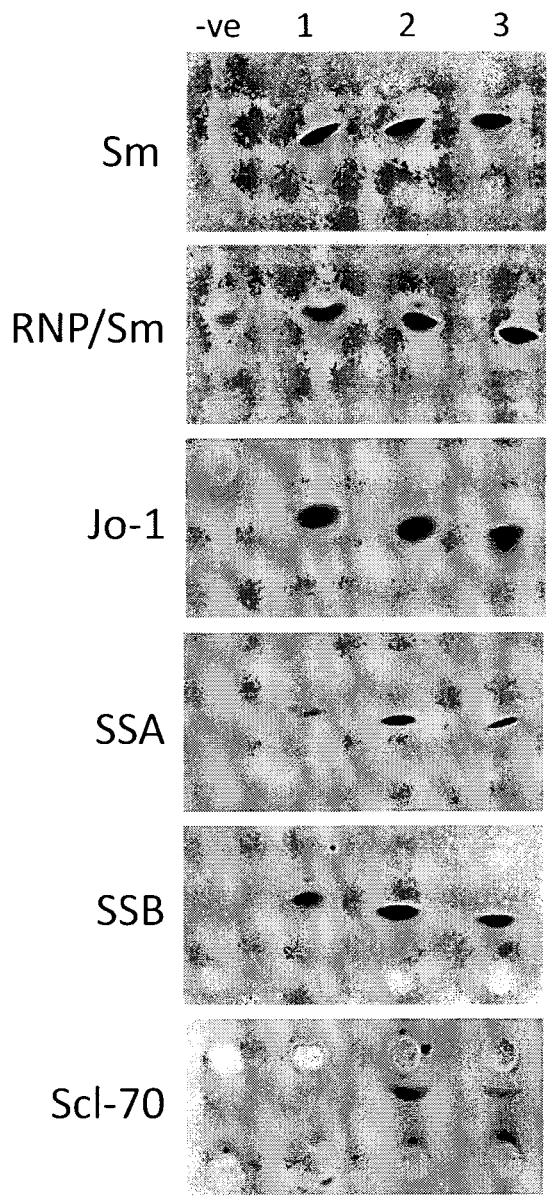

FIG. 8: Counter-immunoelectrophoretic detection of anti-ENA autoantibodies using small molecule fluorescence-labelled autoantigens Fluorescence detection of anti-ENA antibody/small molecule fluorescence-labelled autoantigen precipitins by counter-immunoelectrophoresis. Precipitin formation detected by blue light trans-illumination with amber filter shown for one healthy donor (−ve) and three subject samples with autoantibodies specific for each autoantigen identified in the left hand column.

FIG. 9:

Experimental micro double-diffusion formats for detection of precipitating autoantibodies using fluorescently labelled autoantigens: a) Micro double immunodiffusion format; b) micro counterimmunoelectrophoresis format.

FIG. 10:

Method for preparation of agarose gels for use in CIE. Heated liquid agarose is applied to the recessed area of the mold shown in (A). A support film (GelBond—Lonza, Md., USA) is layered over the agarose. Solidified agarose adheres to the GelBond, which is peeled away from the mold, allowing the gel to be used.

FIG. 11:

Time course for detection of autoantibodies by CIE. DIE gel showing the detection of anti-SSA autoantibodies in patient serum over time. Electrophoresis was at 3 mA constant current. The gel is viewed at the indicated time intervals using blue light trans-illumination with an amber filter.

FIG. 12:

Detection of autoantibodies at different serum dilutions using CIE. Anti-SSA autoantibodies are detected from a range of patient serum dilutions. Autoantibodies are detected at all dilutions tested. Electrophoresis was at 3 mA constant current. The gel was viewed t the indicated time intervals using blue light trans-illumination with an amber filter.

FIG. 13:

Detection of autoantibodies specific for six different nuclear antigens. CIE detection of anti-SSA, SSA/SB, Scl-70, Jo-1, Sm and RNP autoantibodies is shown. Electrophoresis was at 3 mA constant current. The gels were viewed after 60 minutes using blue light trans-illumination with an amber filter.

DETAILED DESCRIPTION OF THE INVENTION

In the description in this specification reference may be made to subject matter which may not be within the scope of the claims of the current application. That subject matter should be readily identifiable by a person skilled in the art and may assist in putting into practice the invention as defined in the claims of this application.

DEFINITIONS

The term "antigen" refers to any substance, including but not limited to a toxin, enzyme, or protein, that stimulates an immune response in the body, especially the production of antibodies. A "target antigen" as used herein refers to an antigen that contains at least one epitope that is specifically bound by a particular target antibody.

An "autoantigen" as used herein refers any endogenous body constituent that stimulates the production of autoantibodies and an autoimmune reaction. An autoantigen is also termed a "self-antigen" as known and used in the art. A "target autoantigen" refers to any endogenous body constituent that has stimulated the production of a particular autoantibody and that contains at least one epitope to which that target autoantibody specifically binds.

As used herein a target antibody and target antigen, including target autoantibodies and target autoantigens, need not be from the same species of organism. What is required is that the target antigen and target autoantigen selectively and specifically bind to each other, wherein the target antigens contain at least one epitope to which the target antibodies specifically bind. For example, a target antigen or target autoantigen according the invention may be obtained from a cow or mouse while the antibody target may be detected from a sample obtained from a human.

The terms "cognate antibody" and "cognate antigen" (including cognate autoantigen) as used herein refer to target antibodies and target antigens that specifically and selectively bind each other. As used herein, cognate antibodies and cognate antigens need not be from the same species of organism. What is required is that the cognate antigen or cognate autoantigen specifically and selectively bind to their respective cognate antibodies and cognate autoantibodies, wherein the cognate antibodies and cognate autoantibodies contain at least one epitope to which the cognate antigens and cognate autoantigens specifically bind. For example, a cognate antigen or cognate autoantigen according the invention may be obtained from a cow, a sheep or a mouse and used to detect, according to the invention, a cognate antibody or cognate autoantibody present in a sample obtained from a human.

A "nuclear autoantigen" as used herein refers to an autoantigen that is at least partially localized in the nucleus of eukaryotic cells.

An "extractable nuclear autoantigen" (ENA) refers to an autoantigen that can be extracted into a liquid phase, typically using high salt concentration, from the nuclei of eukaryotic cells.

The term "antibody" (including target antibody and target autoantibody) refers to an immunoglobulin molecule having a specific structure that interacts (binds) specifically with a molecule comprising the antigen used for synthesizing the antibody or with an antigen closely related to it. As used herein, the term "antibody" broadly includes full length antibodies and may also include certain antibody fragments thereof. Also included are monoclonal and polyclonal antibodies, multivalent and monovalent antibodies, multispecific antibodies (for example bi-specific antibodies), chimeric antibodies, human antibodies, humanized antibodies and antibodies that have been affinity matured.

A "target antigen" that binds "selectively or specifically" to a "target antibody" according to the invention is an antigen that binds preferentially to the target antibody e.g. has less than 25%, or less than 10%, or less than 1% or less than 0.1% cross-reactivity with a non-target antibody. Usually, a target antibody will have a binding affinity (dissociation constant (Kd) value), for the antigen or epitope of no more than $10^{-6}$, or $10^{-7}$M, preferably less than about $10^{-8}$M, more preferably less than about $10^{-9}$M, or $10^{-10}$, or $10^{-11}$ or $10^{-12}$M. Binding affinity may be assessed using surface plasma resonance [see, for example U.S. Pat. No. 7,531,639 or U.S. Pat. No. 6,818,392, each of which is incorporated herein by reference].

Accordingly, a small molecule fluorescence-labelled target antigen or target autoantigen (SMFLTA or SMFLTAA) of or useful in the invention is one that binds selectively or specifically to a "target antibody" or "target autoantibody." An "antigen-binding fragment" or "antibody fragment" (including a target antibody or target antigen binding fragment) refers a portion of the intact antibody that preferably retains most or all, or minimally at least one of, the normal functions of that antibody fragment. An antibody fragment, for example, may comprise an Fc region that retains all or most or some of the function of the corresponding Fc region in the intact antibody. Examples of antibody fragments include Fab, Fab', F(ab')$_2$ and Fv fragments, linear antibodies, diabodies, single chain antibodies (ScFV) and multispecific antibodies.

A "monoclonal antibody" (including a target antibody or target autoantibody) means an antibody that is a highly specific antibody directed against a single epitope on the target antigen. A monoclonal antibody may be obtained from a population of homogenous or substantially homogenous antibodies wherein each monoclonal antibody is identical and/or bind the same epitope, except for natural mutations which may occur in minor amounts.

An "isolated antibody" (including an isolated target antibody or isolated target autoantibody) is an identified antibody which has been separated or recovered, or both, from a component of its natural environment. For example, antibodies that are separated from proteins, including enzymes and hormones or any other body constituents, including cell and tissue constituents. In one embodiment, the antibody is purified to at least 95%, or 96% or 97% or 98% or 99% by weight of antibody. It is believed that suitable methods for determining the purity of an isolated antibody or autoantibody are well known in the art and readily available to the person of skill. Ordinarily the antibody will be prepared by at least one purification step.

A "functional fragment, functional variant or functional derivative" of an SMFLTA or SMFLTAA according to the invention is a labelled antigen or autoantigen that is made up of any subsequence of contiguous amino acid residues that is capable of specifically and selectively binding a target antibody or target autoantibody as described herein. Preferably the binding of the target antibody or target autoantibody results in the formation of an immunoprecipitate (precipitin). Typically such fragments have at least 10, preferably at least 15, more preferably at least 20 amino acids.

A "blood-derived sample" means any sample derived from the blood of a subject to be screened. The sample may be any sample known in the art in which the target antibody or target autoantibody can be detected. Included are samples from any subjects such as from normal healthy subjects with no clinical history of autoimmune disorders as described herein. Blood derived samples include, for example, serum and plasma samples and other sample types, but are not limited thereto.

A level "higher" or "lower" than a control, or a change or deviation from a control in one embodiment is statistically significant. A higher level, lower level, deviation from, or change from a control level or mean control level can be considered to exist if the level differs from the control level by 5% or more, by 10% or more, by 20% or more, or by 50% or more compared to the control level. Statistically significant may alternatively be calculated as P≤0.05. In a further alternative, higher levels, lower levels, deviation, and changes can be determined by recourse to assay reference limits or reference intervals. These can be calculated from intuitive assessment or non-parametric methods. Overall, these methods calculate the 0.025, and 0.975 fractiles as 0.025*(n+1) and 0.975 (n+1). Such methods are well known in the art (Hunt et al., 1997 Clin. Endocrinol. 47:287-296; The Immunoassay Handbook. 3$^{rd}$ edition, ed. David Wild. Elsevier Ltd, 2005).

The presence of a target antibody or target autoantibody that is absent in a control, is also contemplated as a higher level, deviation or change. Absence of a target antibody or target autoantibody that is present in a control is also contemplated as a lower level, deviation or change.

A "statistically significant amount" as used herein describes a mathematical measure of difference between groups. The difference is said to be statistically significant if it is greater than what might be expected to happen by chance alone.

The term "epitope" includes any protein determinant capable of specific binding to an immunoglobulin and/or T cell receptor, that is a site on an antigen to which B and/or T cells respond. Epitopic determinants usually consist of chemically active surface groupings of molecules such as amino acids or sugar side chains, and usually have specific three dimensional structural characteristics, and specific charge characteristics. An epitope typically includes 3, 5 or usually 8-10 amino acids. The amino acids may be contiguous or non-contiguous amino acids juxtaposed by tertiary folding.

As used herein a small molecule fluorophore labelled target antigen (SMFLTA) is a target antigen as defined herein that has been labelled with a small molecule fluorophore where the small molecule fluorophore is detectable by the fluorescence emission of the small molecule upon excitation of the small molecule with the appropriate wavelength of light.

As used herein a small molecule fluorophore labelled target autoantigen (SMFLTAA) is a target autoantigen as defined herein that has been labelled with a small molecule fluorophore where the small molecule fluorophore is detectable by the fluorescence emission of the small molecule upon excitation of the small molecule with the appropriate wavelength of light.

Within the context of a SMFLTA or SMFLTAA according to the invention, the term "small molecule" refers to a compound which has a molecular mass equal to or less than 5000 Daltons (5 kD), preferably less than 3 kD, still more preferably less than 2 kD, and most preferably less than 1 kD. In some cases it is highly preferred that a small molecule have a molecular mass equal to or less than 700 Da. A class of small molecule fluorophore labelled target antigens that are particularly useful according the invention are FITC-labelled target antigen conjugates as commonly known and used in the art. Additional useful fluorophores with similar spectral properties include those with an excitation wavelength of 494 nm and an emission wavelength of 518 nm, but not limited thereto.

Additional fluorophores that may be useful according to the invention include other fluorophores as commonly known and used in the art, including but not limited to those listed in Table 1.

TABLE 1

| Fluorophore | Excitation [nm] | Emission [nm] |
| --- | --- | --- |
| 5-Hydroxytryptamine (HAT) | 370-415 | 520-540 |
| Acridine yellow | 470 | 550 |

TABLE 1-continued

| Fluorophore | Excitation [nm] | Emission [nm] |
|---|---|---|
| Acridine orange | 500 | 530 |
| Alexa Fluor 488 | 494 | 519 |
| Alexa Fluor 532 | 530 | 555 |
| Alexa Fluor 546 | 554 | 570 |
| BODIPY 500/510 | 508 | 515 |
| BODIPY 530/550 | 534 | 554 |
| Cascade Blue | 375 | 410 |
| Coumarin | 384 | 470 |
| CY2 | 489 | 506 |
| CY3 | 548 | 562 |
| CY5 | 650 | 670-700 |
| Dansyl | 340 | 520 |
| DAPI | 345 | 458 |
| DPH | 354 | 430 |
| Erythrosin | 529 | 554 |
| Ethidium Bromide | 510 | 595 |
| FITC | 494 | 518 |
| Fluorescein | 495 | 517 |
| FURA-2 | 340/380 | 500/530 |
| GFP | 395/489 | 509 |
| Hoechst 33258 | 365 | 480 |
| Hoechst 33342 | 355 | 465 |
| Laurdan | 364 | 497 |
| Lucifer yellow CH | 428 | 535 |
| Nile Red | 485 | 525 |
| Oregon Green 488 | 493 | 520 |
| Oregon Green 500 | 503 | 522 |
| Oregon Green 514 | 511 | 530 |
| Prodan | 361 | 498 |
| Pyrene | 341 | 376 |
| Rhodamine 110 | 496 | 520 |
| Rhodamine 123 | 505 | 534 |
| Rhodamine 6G | 525 | 555 |
| Rhodamine B | 540 | 625 |
| SITS | 336 | 438 |
| SNARF | 480 | 600/650 |
| Stilbene SITS, SITA | 365 | 460 |
| Texas Red | 589 | 615 |
| TOTO-1 | 514 | 533 |
| YOYO-1 | 491 | 509 |
| YOYO-3 | 612 | 631 |

The term "specifically associated with a particular autoimmune disorder" when used in reference to an autoantigen as described herein refers to an autoantigen that is known in the art to cause the production, by the body's immune system, of an autoantibody that specifically or selectively binds to at least one epitope of the autoantigen.

The term "specifically associated with a particular autoimmune disorder" when used in reference to an autoantibody as described herein refers to an autoantibody that is known in the art to be produced by body's immune system, in response to an autoantigen as known in the art or described herein, that is specifically or selectively bound, at least one epitope by the autoantibody.

An autoimmune disorder or disease is a disorder or disease that results from the body's production of an inappropriate immune response directed against its own "self antigens". Such responses may be cell or tissue directed or cell or tissue specific. In particular, the immune system may cease to recognize one or more of the body's normal proteins as "self", creating autoantibodies as described herein or as known in the art, which target the body's own cells, tissues, and/or organs. Inflammation and/or damage that results from such attacks may be considered causative of various autoimmune disorders.

For example, an autoimmune disorder may result from an immune response in a normal healthy individual who produces antibodies or T-cells which attack normal cells or tissues displaying proteins normally produced in the body by normal healthy individuals. Prior to this inappropriate immune response, such individuals do not display any clinical phenotype associated with or diagnostic for an autoimmune disease or disorder.

Autoimmune disorders may be categorized into systemic autoimmune diseases and localized autoimmune diseases. Systemic diseases cause damage to many organs whereas localized diseases are those that directly damage only a single organ or tissue. There are, however, no clear and absolute distinctions between these two types of autoimmune disease. It is common for the direct effects of localized autoimmune disease on a single organ or tissue, to extend indirectly to other body organs and systems.

As used herein, "autoimmune disease or disorder" is a condition that occurs when the immune system mistakenly attacks and destroys healthy body tissue. There are more than 80 different types of autoimmune disorders.

The term "autoimmune disorder" as used herein includes, but is not limited to the following diseases or disorders including Acute Disseminated Encephalomyelitis (ADEM), Acute necrotizing hemorrhagic leukoencephalitis, Addison's disease, Agammaglobulinemia, Allergic asthma, Allergic rhinitis, Alopecia areata, Amyloidosis, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Axonal & neuronal neuropathies, Balo disease, Behcet's disease, Bullous pemphigoid, Cardiomyopathy, Castleman disease, Celiac sprue (nontropical), Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block; Coxsackie myocarditis, CREST disease, Essential mixed cryoglobulinemia, Demyelinating neuropathies, Dermatomyositis, Devic's disease (neuromyelitis optica), Discoid lupus, Dressler's syndrome, Endometriosis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Graves' disease, Guillain-Barre syndrome, Hashimoto's disease, Hemolytic anemia, Henoch-Schonlein purpura, Herpes gestationis, Hypogammaglobulinemia, Idiopathic thrombocytopenic purpura (ITP), IgA nephropathy, Immunoregulatory lipoproteins, Inclusion body myositis, Insulin-dependent diabetes (type 1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear. IgA disease (LAD), Lupus (SLE), Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (see Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis; Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal Fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, and Wegener's granulomatosis. Preferably the autoimmune disorder is at least one of, but is not limited to one of, the following common types of autoimmune disorders including Rheumatoid arthritis (RA) and Juvenile RA (JRA) (joints; less commonly lung, skin), Type 1 Diabetes Mellitus (pancreas islets), Lupus [Systemic Lupus Erythematosus] (skin, joints, kidneys, heart, brain, red blood cells, other), Hashimoto's thyroiditis, Graves' disease (thyroid), Scleroderma (skin, intestine, less commonly lung), Celiac disease, Crohn's disease, Ulcerative colitis (GI tract), Sjogren's, syndrome (salivary glands, tear glands, joints), Multiple sclerosis, Goodpasture's syndrome (lungs, kidneys), Addison's disease (adrenal), Wegener's granulomatosis (blood vessels, sinuses, lungs, kidneys), Primary biliary cirrhosis, Sclerosing cholangitis, Autoimmune hepatitis (liver), Polymyalgia Rheumatica (large muscle groups), Temporal Arteritis/Giant Cell Arteritis (arteries of the head and neck), and Guillain-Barre syndrome (nervous system).

As used herein a carrier or diluent of, or useful in the invention is any suitable carrier or diluent as known and used in the art in which the SMFLTA or SMFLTAA of the invention may be resuspended for use.

In a particular embodiment the carrier or diluent may be a buffer that is suitable for use in a DID assay according to methods of the invention as described in Bunn et al. 1993 *Man. Biol. Mark. Dis. A*3:1-12 (Kluwer Academic). The buffer may be any suitable buffer as known and used in the art that has a reasonable ionic strength, for example, 0.1 to 1.0M NaCl, preferably 0.2 to 0.8M NaCl, preferably 0.3 to 0.6M NaCl, preferably 0.4M NaCl, but not limited thereto.

In one non-limiting embodiment, the carrier or diluent may be a buffer that comprises one or all of the following components in suitable amounts: a detergent (e.g., Tween 20), albumin, a preservative (e.g., sodium azide), an anti-oxidant (e.g., dithiothreitol), optionally other salts (including chlorides of potassium, magnesium, ammonium etc. . . . ), and optionally glycerol.

Glycerol is also useful for the stabilisation of antigen components in a kit, for example. It is believed that the formulation of an appropriate buffer, carrier or diluent is within the skill of those in the art.

The term "lyophilize" (including lyophilized, lyophilizes etc. . . . ) (also known as Freeze-drying or cryodesiccation) as used herein refers to a dehydration process typically used to preserve a perishable material or make the material more convenient for transport. Accordingly, a SMFLTA or SMFLTAA or functional fragment, functional variant or functional derivative thereof, according to the invention may be lyophilized to increase stability and shelf life, for example by removing the water from the material and sealing the material in a vial, but not limited thereto. The material may then be easily stored, shipped, and later reconstituted to its original form for use in a method according to the invention.

"Immunoprecipitation" as used herein refers to the technique of precipitating an antibody out of solution using an antigen that specifically or selectively binds to that particular antibody.

As an aside immunoprecipitation also refers to precipitating an antigen by reacting with specific antibody and then adding a solid phase reagent (typically Protein A coupled to agarose beads) that will lead to sedimentation of the antigen-antibody complex In particular, an immunoprecipitation according to the invention is the precipitation of a target antibody, including a target autoantibody, due to the specific or selective binding of a target antigen, including a target autoantigen, to the target antibody, in a cross-linked complex. The formation of the cross-linked complex results at an interface formed by the diffusion of the target antibody and the target antigen through a gel matrix, preferably an agarose gel matrix, due to the presence of equivalent concentrations of the target antibody and target antigen.

The terms "immunoprecipitate" and "precipitin" are used interchangeably and mean the complex of cross-linked target antibodies and target antigens (including target autoantibodies and target autoantigens) that is formed as the result of an immunoprecipitation.

As used herein, an immunoprecipitation device refers to any device that is configured to allow cognate antigens and cognate autoantigens and their respective cognate antibodies and autoantibodies as described herein to react under suitable conditions to form an immunoprecipitate or precipitin.

A micro-immunodiffusion device as used herein refers to an immunoprecipitation device configured to allow cognate antigens and cognate autoantigens and their respective cognate antibodies and autoantibodies as described herein to react under suitable conditions to form an immunoprecipitate or precipitin. In one example, a micro-immunodiffusion device comprises a body, which may be, but is not limited to a modified microscope slide having a primary well containing a gel diffusion medium through which a target antibody and target antigen (including a target autoantibody and target autoantigen) can diffuse to form an immunoprecipitate. Preferably the gel diffusion medium is an agarose gel diffusion medium, but is not limited thereto. The primary well comprises a series of secondary wells that are configured to accept test samples and SMFLTAs or SMFLTAAs of the invention. The configuration of the wells in combination with the gel strength and buffer concentration of the gel diffusion medium allows diffusion of the test sample and the SMFLTAs or SMFLTAAs through the gel diffusion medium to form a precipitin. Precipitin formation occurs at an interface where the concentrations of the antibodies to be detected (including autoantibodies) and the SMFLTAs or SMFLTAAs according to the invention are present at equivalent concentrations.

"Counter-immunoelectrophoresis" (CIE) refers to a laboratory technique that employs an electric current to accelerate the migration of antibody and antigen through a buffered gel diffusion medium. Antigens, including autoantigens, in a buffered gel diffusion medium having a controlled pH, are strongly negatively charged, whereas antibodies, including autoantibodies in the same medium are less negatively charged. Preferably the gel diffusion medium is an agarose gel diffusion medium, but is not limited thereto. Upon application of a suitable electric current, antigens will migrate rapidly across the electric field toward the anode, whereas antibodies will migrate in the opposite or 'counter' direction toward the cathode. Precipitin formation will occur where antibodies and their cognate antigens combine to form a cross-linked complex.

In one embodiment according to the invention, test serum samples obtained from subjects having or suspected of having an autoimmune disorder, are placed in the anodal wells of a gel comprised in, or part of, a CIE assay device. The CIE assay device is a type of immunoprecipitation device as described herein. The test samples are electrophoresed at a suitable voltage for a specified period of time to allow antibodies, including autoantibodies, present in the test samples to move into the gel to reach a predetermined location. A SMFLTA or SMFLTAA of the invention is placed in the cathodal wells of the gel and the gel again electrophoresed at a suitable voltage for a specified period of time to allow the SMFLTA or SMFLTAA to contact the antibodies or autoantibodies present in the test samples and form a precipitin as described herein.

For example, a suitable voltage may be 50V and a specified amount of time may range from about 5 to about 120 minutes, from about 10 to 120 minutes, and including, but not limited to, about 6, 7, 8, 9, 10, 15 20, 30, 40, 50, 60, 70, 80, 90, 100, or about 110 minutes. In some instances, a specified amount of time may exceed 120 minutes. The choice of a suitable voltage and specified amount of time, that will allow the SMFLTA or SMFLTAA according to, or used in the methods of the invention, to contact any antibodies or autoantibodies present in the test samples and form a precipitin, is believed to be well within the skill of those in the art.

Following electrophoresis, precipitins bands are formed in the CIE assay device are visualized by blue light trans-illumination of the gel viewed through an amber filter. Trans-illumination may be performed as known in the art, for example, using a microscope, or a gel documentation system or other type of gel reader, equipped with the appropriate fluorescence filter sets.

Figure 9:
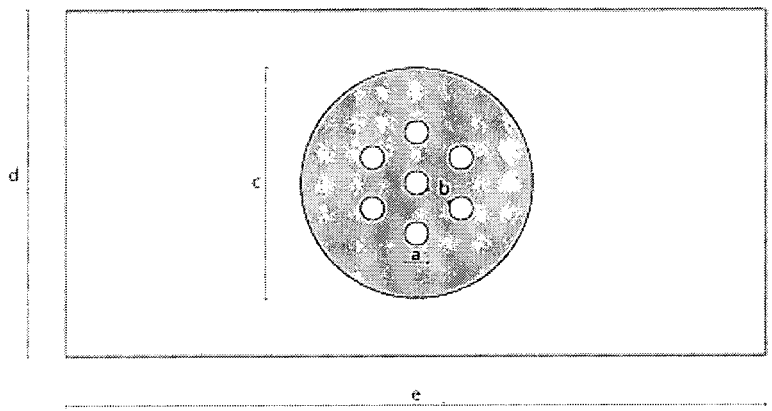
Figure 9:
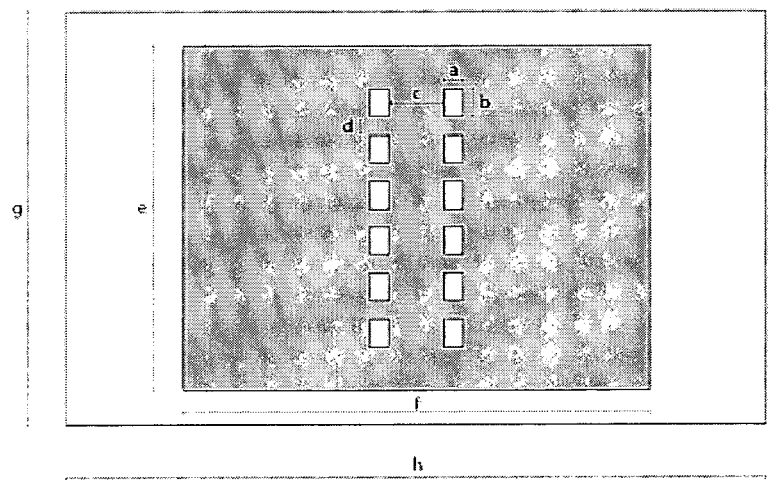
Figure 10:
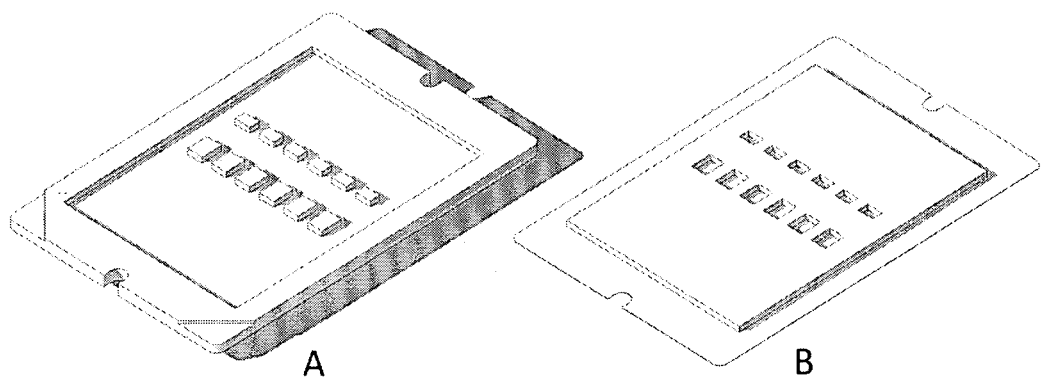

In one non limiting embodiment, a CIE assay according to the invention may be performed using a microcounterelectrophoresis (microCIE) format (FIGS. 9b and 10). A gel, for example an agarose gel of appropriate gel strength and buffer concentration (shaded area) is cast into a rectangular recess in a suitable support material to yield a suitable gel depth. Preferably the rectangular recess is a 37.5×50 mm rectangular recess and the gel depth is of 2 mm, but the recess and gel depth are not limited thereto. The suitable support material has been configured, for example, as a CIE assay plate or other assay CIE device. The support material in which the recess has been formed, for example, during the construction of the plate or device, or by subsequent machining, but not limited thereto, can be made of any suitable support material including but not limited to various acrylic polymers, polystyrene(s), or methacrylate (s), and the like. In one embodiment, the support material is configured as or from a clear acrylic sheet.

The gel is configured to contain sample wells that may, for example, be formed when the gel is cast. The wells may also, for example, be excised from the cast gel and extracted using a metal tube attached to a suction device. Serum samples obtained from a subject to be tested (i.e., containing a target antibody) are added to the column of wells on the left, and a target antigen (including, for example, a SMFLTA or SMFLTAA of the invention) is added to the column of wells on the right. A suitable electrical current is applied through a cathode contacted with the left hand side of the gel (beyond the subject sample wells) and an anode contacted with the right hand side of the gel (beyond the antigen wells).

For example, the subject samples placed in the anodal wells are electrophoresed at the suitable voltage for a specified period of time to allow antibodies, including autoantibodies, present in the test samples to move into the gel to reach a predetermined location. A SMFLTA or SMFLTAA of the invention placed in the cathodal wells of the gel is then electrophoresed at a suitable voltage for a specified period of time to allow the SMFLTA or SMFLTAA to contact the antibodies or autoantibodies present in the test samples and form a precipitin as described herein.

Several non-limiting embodiments of a CIE assay according to the invention are presented as Examples 7 and 8. According to the method shown in Example 8, detection of precipitating antibodies, including autoantibodies, can be carried out in as little as about 10 minutes.

"Double immunodiffusion (DID; also known as "Ouchterlony double immunodiffusion" or "agar gel immunodiffusion" is a relatively simple method that can be used for the detection of extractable nuclear antigens (ENAs). DID is performed using a gel diffusion medium that contains a series of wells. In one example of a DID assay according to the invention, the wells are configured with a single central well surrounded by a series of peripheral wells. The peripheral wells may be placed symmetrically around the central well. Alternatively the peripheral wells of different sizes are placed around the central well.

In one non-limiting embodiment, the DID assay may be set up using a microDID format (FIG. 9a). An appropriate gel medium, for example an agarose gel of an appropriate gel strength and buffer concentration (shaded area) (but not limited thereto) can be cast into a recess in a suitable support material to yield a suitable gel depth. In one example the recess is circular, but is not limited thereto. The suitable support material has been configured as a DID assay plate or other DID assay device. The support material in which the recess has been formed, for example, during the construction of the plate or device, or by subsequent machining, but not limited thereto, can be made of any suitable support material including but not limited to various acrylic polymers, polystyrene(s), or methacrylate (s), and the like. In one embodiment, the support material is configured from or as a clear acrylic sheet.

In an example using a circular recess, the circular recess contained or formed within in the support material is of any suitable diameter, for example, a 25 to 50 mm diameter circular recess, preferably 25 mm. The gel depth formed by the gel cast in the circular recess is likewise of any suitable depth. What is important in this embodiment is that the diameter of the circular recess and the depth of the gel are appropriate to allow for diffusing target antigens and target antibodies (including target autoantigens and target autoantibodies) to come into contact and form a detectable precipitin under the chosen reaction conditions. Suitable gel depths may be, for example from 0.5 to 5 mm, preferably 1 to 4 mm, more preferably 1.5 to 3 mm, more preferably 2 mm.

Wells are cut in the gel formed in the circular recess, for example as shown in FIG. 9a. The excised gel is removed from the wells using a metal tube attached to a suction device. Serum samples obtained from a subject to be tested are added to the outer wells, and a target antigen, including but not limited to a SMFLTA or SMFLTAA of the invention, is added to the central well. The serum samples may be diluted or undiluted as known in the art or as described herein.

The antibodies to be detected from the test sample and the target antigens are then allowed to diffuse through the gel diffusion medium for a suitable amount of time to form a precipitin. Precipitin formation occurs at an interface where the concentrations of the antibodies to be detected and the target antigens are present at equivalent concentrations.

In one embodiment according to the invention, test serum samples obtained from subjects having or suspected of having an autoimmune disorder, are placed in the peripheral wells. A SMFLTA or SMFLTAA of the invention is placed in the central well. The test samples and SMFLTA or SMFLTAA are allowed to diffuse through the buffered gel diffusion medium for a suitable amount of time such that precipitins as described herein are formed. For example, a suitable amount of time may be 24 to 48 hours, but is not limited thereto.

In some instances, more than one peripheral well may be used, which leads to multiple possible outcomes based on the reactivity and specificity of the antigen and antibody (including autoantigens and autoantibodies) selected. The zone of precipitin formation may indicate a full identity (i.e. a continuous line), partial, identity (i.e. a continuous line with a spur at one end), or a non-identity (i.e. the two lines cross completely) of the selected antigen/antibody combination.

Without wishing to be bound by any theory, the applicant believes that precipitin formation takes place due to the multivalent character of most antigens (including autoantigens). Typically an antigen has several antigenic determinants which allow binding of multiple antibodies. Typically, antibodies, including autoantibodies, have at least two antigen binding sites. In some cases, e.g., the case of IgM, there may be up to 10 antigen binding sites. Due to these multiple sites, large aggregates or cross-linked complexes of antigens and antibodies may be formed.

An increase in the amount of antigen relative to a constant amount of antibody allows for essentially all of the target antibodies in a given test sample to be bound by the antigen into the precipitin. Preferably, all of the target antibodies in a given test sample are bound by the antigen into the precipitin. This is called the antibody-excess zone (i.e. prozone phenomenon). For example, as the concentration of a given antigen increases due to diffusion through the gel diffusion medium, the amount protein precipitated in the cross-linked complexes will increase. A 'zone of equivalence" or "equivalence point" will be formed once the ratio of antigen/antibody is optimal. Where the amount of antigen diffusing through the gel diffusion medium exceeds the amount of antibody, the precipitin formation will decrease, leading to an "antigen excess zone".

"Substantially the same binding characteristics" refers to an antibody or antigen that is a functional fragment, functional variant or functional variant of an target antibody, autoantibody, antigen or autoantigen as described herein that has essentially the same binding selectivity and sensitivity as another antibody, autoantibody, antigen or autoantigen to which the first antibody, antigen, autoantibody or autoantigen is compared. Typically such a molecule that has substantially the same binding characteristics will share sufficiently similar three dimensional polypeptide structure to retain essentially the same binding selectivity and sensitivity as the molecule to which it is compared. Preferably, essentially the same binding selectivity or sensitivity is the same binding selectivity or sensitivity.

The term "biological sample" is used interchangeably herein with the term "test sample" and refers to any sample obtained from a subject to be screened. Preferably the subject to be screened has or is suspected of having an autoimmune disorder. The test sample may be any sample known in the art in which a target antibody or target autoantibody of interest may be detected. Included are any body fluids such as plasma, blood, saliva, interstitial fluid, serum, urine, synovial, cerebrospinal, lymph, seminal, amniotic, pericardial fluid and ascites. Included are samples from any subjects such as those subjects displaying a clinical phenotype suggestive of or indicative of an autoimmune disease or disorder, but not limited thereto. Also included are control samples that may be from normal healthy subjects with no clinical history of autoimmune disease or disorder or that may be artificial samples containing a known amount of a target antibody or target autoantibody that is known to be non-reactive (e.g., non-binding) with a target antigen or target autoantigen that is labelled to yield the SMFLTAs or SMFLTAAs of the invention.

Test samples that may be used in the methods according to the invention can be obtained from any source. For example, in one embodiment, the test samples are obtained from an animal, preferably a bird or a mammal, more preferably a mammal. Preferably the mammal includes human and non-human mammals such as cats, dogs, horses, pigs, cows, sheep, deer, mice, rats, primates (including gorillas, rhesus monkeys and chimpanzees), possums and other domestic farm or zoo animals, but not limited thereto. Preferably, the mammal is a cow or a sheep. Preferably the mammal is a human.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "polypeptide", as used herein, encompasses amino acid chains of any length of a specified polypeptide sequence or any combination thereof, wherein the amino acid residues are linked by covalent peptide bonds. The term may refer to a polypeptide that is a purified natural product, or that has been produced partially or wholly using recombinant or synthetic techniques. The term may refer to an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity or binding and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the required peptide function.

As used herein, the term "variant" refers to a target antibody, target antibody, target antigen or target autoantigen amino acid sequence which is different from a specifically identified sequence, wherein one or more amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the target antibodies, target autoantibodies, target antigens or target autoantigens useful in the invention have biological activities that are the same or substantially similar to those of the parent target antibodies, target autoantibodies, target antigens or target autoantigens. The term "variant" with reference to target antibodies, target autoantibodies, target antigens or target autoantigens encompasses all forms of target antibodies, target autoantibodies, target antigens or target autoantigens as defined herein.

The term "variant" with reference to target antibodies, target autoantibodies, target antigens or target autoantigens also encompasses naturally occurring, recombinantly and synthetically produced target antibodies, target antigens, target autoantigens or polypeptides. Variant target antibody, target autoantibody, target antigen or target autoantigen sequences preferably exhibit at least 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and preferably at least 99% identity to a target antibody, target autoantibody, target antigen or target autoantigen sequence useful in the present invention. Identity is found over a comparison window of at least 5 amino acid positions, preferably at least 7 amino acid positions, preferably at least 10 amino acid positions, preferably at least 15 amino acid positions, preferably at least 20 amino acid positions and most preferably over the entire length of a target antibody, target autoantibody, target antigen, or target autoantigen used in the invention.

Target antibody, target autoantibody, target antigen or target autoantigen variants also encompass those which exhibit a similarity to one or more of the specifically identified target antibodies, target antigens, target autoantigens or polypeptide sequences that is likely to preserve the functional equivalence of those sequences and which could not reasonably be expected to have occurred by random chance.

Polypeptide sequence identity and similarity can be determined in the following manner. The subject polypeptide sequence is compared to a candidate polypeptide sequence using BLASTP (from the BLAST suite of programs, version 2.2.14 [May 2006]) in bl2seq, which is publicly available from NCBI (ftp://ftp.ncbi.nih.gov/blast/). The default parameters of bl2seq are utilized except that filtering of low complexity regions should be turned off.

The similarity of polypeptide sequences may be examined using the following UNIX command line parameters:

$bl2seq\ -i\ peptideseq1\ -j\ peptideseq2\ -F\ F\ -p\ blastp$

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Variant polypeptide sequences preferably exhibit an E value of less than $1\times10^{-5}$, more preferably less than $1\times10^{-6}$, more preferably less than $1\times10^{-9}$, more preferably less than $1\times10^{-12}$, more preferably less than $1\times10^{-15}$, more preferably less than $1\times10^{-18}$ and most preferably less than $1\times10^{-21}$ when compared with any one of the specifically identified sequences.

Polypeptide sequence identity may also be calculated over the entire length of the overlap between a candidate and subject polypeptide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

A variant target antibody, target autoantibody, target antigen, or target autoantigen includes target antibodies, target autoantibodies, target antigens or target autoantigens wherein the amino acid sequence differs from the sequence of a non-variant target antibody, target autoantibody, target antigen, or target autoantigen by one or more conservative amino acid substitutions, deletions, additions or insertions which do not affect the biological activity of the target antibody, target autoantibody, target antigen, or target autoantigen. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine. Examples of conservative and semi-conservative substitutions can be taken from Table 2 below.

TABLE 2

| Original Residue | Exemplary Substitutions | Preferred Substitution |
|---|---|---|
| Ala (A) | val; leu; ile; pro | val |
| Arg (R) | lys; gln; asn | lys |
| Asn (N) | gln; his; lys; arg | gln |
| Asp (D) | glu | glu |
| Cys (C) | ser | ser |
| Gln (Q) | asn; his | his |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | phe; val |
| Lys (K) | arg; gln; asn | arg |
| Met (M) | leu; phe; ile | leu |
| Phe (F) | leu; val; ile; ala; tyr | val |
| Pro (P) | ala | ala |
| Ser (S) | Thr; gly | gly |
| Thr (T) | ser; ala; pro | ser; ala |
| Trp (W) | tyr; phe | tyr |
| Tyr (Y) | trp; phe; thr; ser | phe |
| Val (V) | ile; leu; met; phe; ala; norleucine | leu |

Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his lys, arg:
(5) residues that influence chain orientation: gly, pro; and
(6) aromatic: trp, tyr, phe.

Non-conservative substitutions will entail exchanging a member of one of these classes for a member of another class.

Substitutions, deletions, additions or insertions may be made by mutagenesis methods known in the art. A skilled worker will be aware of methods for making phenotypically silent amino acid substitutions. See for example Bowie et al., 1990, Science 247, 1306.

"Subject" as used herein is preferably an animal. Preferably the animal is a mammal. Preferably the mammal includes human and non-human mammals such as cats, dogs, horses, pigs, cows, sheep, deer, mice, rats, primates (including gorillas, rhesus monkeys and chimpanzees), possums and other domestic farm or zoo animals, but not limited thereto. Preferably, the mammal is human.

The term "clinical phenotype" as used herein refers to the complete observable characteristics of a subject having or suspected of having a particular disease or disorder, for example, an autoimmune disorder. These characteristics include all anatomic, physiologic, biochemical, and behavioural traits, as determined by the interaction of genetic makeup and environmental factors. Generally speaking symptoms of an autoimmune disease vary widely and depend on the specific disease. A group of symptoms that can occur with autoimmune diseases may include dizziness, fatigue, and general ill-feeling and/or low grade fever.

An "enzyme linked immunosorbent assay (ELISA)", also known as an enzyme-linked immunoassay; EIA as used herein takes its regular meaning as known and used in the art. In general terms, an ELISA is an assay that relies on an enzymatic conversion reaction and is used to detect the presence of specific substances including, but not limited to enzymes, viruses, antibodies, and bacteria.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

Small Molecule Fluorescence-Labelled Target Antigens and Autoantigens

The work as detailed herein gives rise to numerous aspects of the invention relating to the detection of target antibodies, including target autoantibodies, providing, for example, compositions comprising small molecule fluorescence labelled target antigens and target autoantigens (SMFLTAs or SMFL-TAAs) which may be used in the methods of the invention as described herein. Also included are kits which employ SMFLTAs or SMFLTAAs for use in these methods.

The target antigens and target autoantigens that are fluorescently labelled as SMFLTAs or SMFLTAAs according to the invention and that are subsequently used in the methods of the invention as detailed herein are preferably isolated. They may be isolated or purified from natural sources using a variety of techniques that are well known in the art (e.g. Deutscher, 1990, Ed, Methods in Enzymology, Vol. 182, Guide to Protein Purification,). Technologies include HPLC, ion-exchange chromatography, and immunochromatography but are not limited thereto.

In one embodiment, target antigens or target autoantigens, including functional fragments, functional variants and functional derivatives thereof, may be prepared by any standard means as commonly known and used in the art.

For example, the target antigens, target autoantigens or functional fragments, functional variants and functional derivatives thereof may be isolated from natural sources, including but not limited to animals. Preferably the animals are birds or mammals. Preferably the mammal includes human and non-human mammals such as cats, dogs, horses, pigs, cows, sheep, deer, mice, rats, primates (including gorillas, rhesus monkeys and chimpanzees), possums and other domestic farm or zoo animals, but not limited thereto. Preferably, the mammal is a cow or a sheep. Preferably the mammal is a human.

Alternatively the target antigens and autoantigens may be expressed recombinantly in suitable host cells and separated from the cells using standard techniques of molecular biology as known and used in the art Sambrook et al., (supra).

For example, host cells comprising expression cassettes and vectors comprising polynucleotides encoding a target antigen, target autoantigen, or functional fragment, functional variant or functional derivative thereof to be labelled as a SMFLTA or SMFLTAA according to the invention are useful in methods for recombinant production of polypeptides. Methods for producing recombinant proteins are well known in the art and are described generally in Sambrook et al., (supra), and Ausubel et al., Current Protocols in Molecular Biology, Greene Publishing, 1987. Methods for transforming selected host cells with the vectors are also known, for example, the calcium chloride treatment described by Cohen, S N; PNAS 69, 2110, 1972.

Methods of producing recombinant polypeptide commonly involve the culture of host cells in an appropriate medium in conditions suitable for or conducive to, expression and selection of a polypeptide of interest. Cells with a selectable marker may additionally be grown on medium appropriate for selection of host cells expressing a polypeptide of interest. Transformed host cells expressing a polypeptide of interest are selected and cultured under conditions suitable for expression of the polypeptide. The expressed recombinant polypeptide, may be separated and purified from the culture medium using methods well known in the art including ammonium sulfate precipitation, ion exchange chromatography, gel filtration, affinity chromatography, electrophoresis and the like (e.g. Deutscher, Ed, 1990, Methods in Enzymology, Vol 182, Guide to Protein Purification). Host cells may also be useful in methods for production of a product generated by an expressed polypeptide of interest.

For example, various host cells can be used for recombinant production of a target antigen, target autoantigen, or functional fragment, functional variant or functional derivative thereof, to be labelled as a SMFLTA or SMFLTAA according to the invention, from an expression cassette or vector. Such host cells may be derived from prokaryotic or eukaryotic sources, for example yeast, bacteria, fungi, insect (e.g. baculovirus), animal, mammalian or plant organisms. In one embodiment the host cells are isolated host cells. Prokaryotes most commonly employed as host cells are strains of *E. coli*. Other prokaryotic hosts include *Pseudomonas, Bacillus, Serratia, Klebsiella, Streptomyces, Listeria, Saccharomyces, Salmonella* and *Mycobacteria* but are not limited thereto.

Eukaryotic cells for expression of recombinant protein include but are not limited to Vero cells, HeLa, CHO (Chinese Hamster ovary cells), 293, BHK cells, MDCK cells, and COS cells as well as prostate cancer cell lines such as PrEC, LNCaP, Du 145 and RWPE-2. These cells are available from ATCC, Virginia, USA.

In one embodiment, a method of making a target antigen, target autoantigen, or functional fragment, functional variant or functional derivative thereof, to be labelled as a SMFLTA or SMFLTAA according to the invention comprises the steps of transforming a host cell with an expression cassette or vector that comprises a polynucleotide sequence encoding the a target antigen, target autoantigen, or functional fragment, functional variant or functional derivative thereof, culturing the host cell under conditions whereby the target antigen, target autoantigen, or functional fragment, functional variant or functional derivative thereof is expressed and subsequently isolating the expressed target antigen, target autoantigen, or functional fragment, functional variant or functional derivative thereof.

Generally speaking, a number of target antigens, target autoantigens, or functional fragments, functional variants or functional derivatives thereof that may be suitably labelled to form the SMFLTA or SMFLTAA according to the invention or that may be used in the compositions or methods of the invention may be obtained from commercial suppliers including: AROTEC Diagnostics Limited (Lower Hutt, New Zealand; www.arodia.com). Immunovision, Inc. (Springdale, Ark., USA www.immunovision.com); The Antigen Site (San Diego, Calif., USA www.antigensite.com).

Preparation of Labelled Target Antigens and Target Autoantigens

The target antigen or target autoantigen of or useful in accordance with the invention comprises at least a functional fragment, functional derivative or functional variant of a target antigen or target autoantigen of interest that has been chemically labelled with a small molecule fluorophore. A chemically labelled small molecule fluorescent target antigen or autoantigen retains substantially all, preferably all, the selectivity and sensitivity of binding of the un-labelled target antigen or autoantigen for its target or cognate antibody or autoantibody.

In one embodiment, the SMFLTA or SMFLTAA according to the invention is labelled with any suitable small molecule fluorophore selected on the basis of its spectral properties, which are preferably similar to fluorescein isothiocyanate (FITC). This means that the small molecule fluorophore can be detected using the same equipment as that used to detect FITC.

FITC is commonly used in the detection of autoantibodies by immunofluorescence microscopy. This compound has an excitation maximum at wavelength 495 nm and an emission maximum at wavelength 517 nm, and is usually detected using an appropriate excitation filter/barrier filter combination. Many such small molecule fluorophores are available and will be known to the person of skill in the art (e.g., Miller L. W. (ed.) Probes and Tags to Study Biomolecular Function: for Proteins, RNA, and Membranes, 2008. pp 193; Haugland R. P. (ed.): The Handbook. A Guide to Fluorescent Probes and Labelling Technologies $10^{th}$ ed., 2005 (Invitrogen Corp.)

For example, the small molecule fluorophore may be an FITC derivative, including but not limited to, AlexaFluor 488 or DyLight 488, that has been tailored for various chemical and biological applications where greater photostability, higher fluorescence intensity, and/or different attachment groups are needed. Additional examples of fluorophores which may be suitable for use in producing a SMFLTA or SMFLTAA of or useful in the invention may be found listed in Table 1.

In one non-limiting embodiment, fluorophores can be covalently attached to target antigens or target autoantigens through a process referred tows conjugation. In conjugation, the fluorophore is covalently attached through reaction with an accessible amino acid side chain group of the target antigen. Typically a reactive derivative of the fluorophore is presented to the target antigen. A number of different fluorophore derivatives that react with various reactive groups on target antigens (including autoantigens) are known in the art and may be used according to the invention. For example fluorophore derivatives that react with target antigen amine groups can include isothiocyanates, succinimidyl esters, sulfosuccinimidyl esters, tetrafluorophenyl esters, carbonyl azides and sulfonyl chlorides; fluorophore derivatives that react with target antigen thiol groups can include iodoacetamides, maleimides, alkyl hydrides and arylating agents; and fluorophore derivatives that react with target antigen alcohol groups that have been oxidized with periodate to yield aldehydes can include hydrazine, hydroxylamine or amine derivatives.

In addition, to be a suitable substitute small molecule fluorophore, covalent modification of the target antigen or autoantigen must not significantly alter the selectivity and specificity of the target antigen or target autoantigen for its target antibody.

Detection of Target Antibodies

The applicants have determined that SMFLTAs or SMFLTAAs can be used effectively for sensitive and selective detection of target antibodies in an immunodiffusion type of assay.

The applicant has found that fluorescent labeling of target antigens and autoantigens, using small molecules as described herein, has no significant effect on the binding characteristics of the labelled antigens for their cognate antibodies. This observation is at odds with established views of antigen/antibody binding characteristics. Generally, the art of immunology, particularly immunodetection, considers that even minor changes in antigen or antibody structure can have significant effects on binding characteristics.

The generally accepted view in this art is that covalent modification of amino acids that are important for determining the three dimensional structure of antibodies and antigens can lead to loss or reduction of antibody/antigen reactivity (i.e., selectivity and specificity). This loss or reduction is particularly evident when such covalent modification is within regions of antigenic determination (i.e., epitopes and epitope binding regions).

In direct contradiction of this, the applicant has shown that the attachment of a small molecule fluorophore to an antigen, particularly an autoantigen, constitutes a covalent modification that does not result in the loss or reduction of antibody/antigen reactivity. Without wishing to be bound by any theory, the applicant believes that this is because amino acids that are important for autoantigen epitopes are not modified, or if they are that this modification is sufficiently tolerated such that no significant reduction of reactivity with cognate autoantibodies is observed.

The applicant has shown for the first time that small molecule fluorescence-labelled autoantigens can be used to specifically detect autoantibodies in a sample suspected of containing autoantibodies with a selectivity and sensitivity of detection that minimizes both false positive and/or false negative results when compared to autoantibody detection using standard immunoprecipitation assay formats, including standard DID, counter-immunoelectrophoresis and ELISA.

The applicant has further shown that SMFLTAAs according to the invention can be used in diffusion type immunoassays to fluorescently detect and semi-quantify autoantibodies in a sample containing or suspected of containing autoantibodies. Preferably the diffusion type immunoassay is a double immunodiffusion assay or counter-immunoelectrophoresis assay as described herein. Preferably the double immunodiffusion assay or counter-immunoelectrophoresis is carried out in an immunoprecipitation device. More preferably the immunodiffusion device is a micro-immunodiffusion device according to the invention.

The detection of autoantibodies according to the applicant's methods can be performed with greater sensitivity than can be achieved with standard DID immunoprecipitation assays as currently employed in the art. For example, the applicant has shown that the sensitivity of detection may be increased by up to ten fold using their methods (FIG. 4).

Detection of autoantibodies according the invention can also be carried out with fewer false positive results as compared to ELISA. Without wishing to be bound by any theory, the applicant believes that this is because ELISA is a particularly sensitive-technique. ELISA is therefore known to return weakly positive results, termed "borderline" or "grey area" low positive results. Frequently, such results are not consistent with clinical presentation and are subsequently determined to be "false" positive results.

Accordingly, the SMFLTAs or SMFLTAAs used in the methods according to the invention can provide a more accurate diagnosis of numerous autoimmune diseases in a subject, while avoiding the problems associated with the need for further confirmatory testing of the subject, including the expense of further testing and the general inconvenience.

In one embodiment, the concentration of an antibody, including an autoantibody, may be determined semi-quantitatively from a sample using a SMFLTA or SMFLTAA and the applicant's methods according to the invention. Such a determination is made by measuring the fluorescence intensity of the SMFLTA or SMFLTAA bound in a precipitin according to the methods of the invention.

The term, "semi-quantitatively" as used herein refers to a quantification that yields an approximation of the quantity or amount of a substance; between a qualitative and a quantitative result.

Fluorescent autoantigen complexes, e.g. precipitins formed according to the invention can be detected in using a range of equipment configurations. Suitable equipment that can be used to detect and measure the fluorescence intensity of a SMFLTA or SMFLTAA bound in a precipitin according to the invention includes, but is not limited to a Gel Doc XR System (BioRad, CA) with retrofitted with a SafeImager™ blue-light transilluminator (Invitrogen, CA) with an amber emission screen; a Nikon Eclipse 80i immunofluorescence microscope with a B-2e/C filter set, a Fujifilm FLA-5100 laser scanner with a 532 emission filter set. As will be appreciated, any suitable imaging system may be used or may be adapted for use, with the methods according to the invention, including numerous other systems that are well known to the person of skill in the art and commonly available in research laboratories.

The practitioner of the invention as described herein thereby avoids the additional costs and/or inconvenience associated with a requirement for obtaining specialized equipment in order to practice the invention, beyond what would commonly be present in a standard clinical or research laboratory as known in the art.

Image analysis, including semi-quantification of fluorescence intensity may be carried out using any appropriate imaging software, including but not limited to QuantityOne software (BioRad, CA), ImageQuant™ software (GE Healthcare, NJ), and/or NIS Elements software (Nikon, NY).

Use of the applicant's SMFLTA or SMFLTAA in methods according to the invention is also advantageous in being much simpler to perform (DID) or much faster to perform (CIE), or both, than ELISA methods. In addition, DID and CIE methods according to the invention are much faster than current methods, do not require staining and are more sensitive than conventional DID or CIE.

Based on their surprising findings, the applicants provide numerous aspects of an invention relating to an improved method of detecting antibodies, particularly autoantibodies, in a sample obtained from a subject having or suspected of having an autoimmune disease or disorder.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention will now be illustrated in a non-limiting way by reference to the following examples.

EXAMPLES

Double immunodiffusion (DID) and counter-immunoelectrophoresis (CIE) detailed in the following examples was performed according to Bunn & Kveder 1993. DID was performed for 24 hours on 0.8% agarose gels with 2.5 mm sample wells that were 3.0 mm apart. CIE was performed on 1.0% agarose gels with sample wells that were 5.0 mm apart.

Example 1

Small Molecule Fluorescence-Labelling of a Target Antigen

The following example uses commercially available, purified Ro60 SSA antigen (also referred to herein as "SSA") available from AROTEC Diagnostics Limited (Lower Hutt, New Zealand; www.arodia.com).

Purified SSA was dialysed into 0.1 M carbonate buffer, pH 9.0; 0.4 M NaCl and then reacted with fluorophore AlexaFluor 488 carboxylic acid, succinimidyl ester according to the manufacturer's instructions (The Handbook. A Guide to Fluorescent Probes and Labelling Technologies. MTZ Spence (ed) 2005 by Invitrogen Corp.). This fluorophore was selected based on spectral properties that are similar to those of fluorescein isothiocyanate (FITC). This fluorophore has an excitation maximum at wavelength 495 nm and an emission maximum at 517 nm. AlexaFluor 488 can therefore be detected using readily available laboratory techniques and devices, including, for example, epi-fluorescence microscopy and/or fluorescence plate readers, designed and equipped to detect FITC fluorescence.

Un-reacted fluorophore was separated from labelled antigen by gel filtration. Sodium dodecyl sulphate polyacrylamide gel electrophoresis (SDS-PAGE) was performed according to Laemmli (Nature 220 (1970) 680). The separation gel contained 13.5% acrylamide. After electrophoresis, proteins were detected by Coomassie blue staining, or were immunoblotted by transferring to nitrocellulose membrane and then probed using subject serum and anti-IgG alkaline phosphatase conjugate according to Towbin et al. (Proc. Natl. Acad. Sci. USA 76 (1979) 4350).

Figure 1:
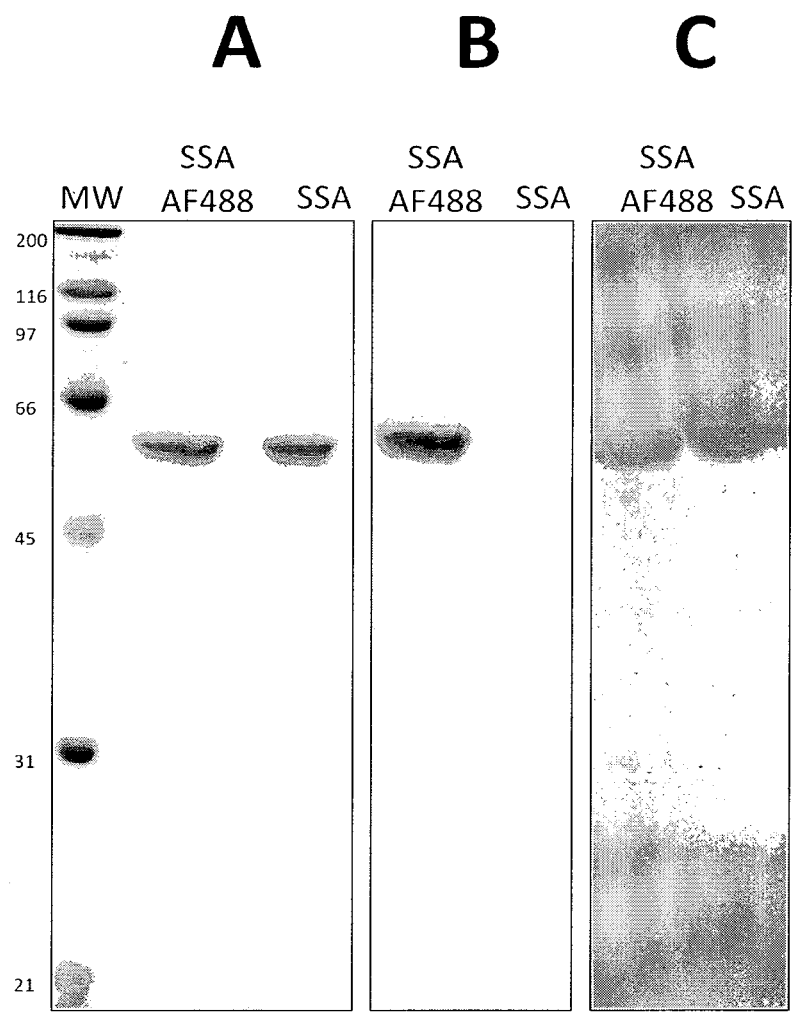
FIG. 1: Fluorescent labelling of (Ro60) SSA antigen

The separation of AlexaFluor 488-labelled and unlabelled SSA antigen (1.0 μg of each) by SDS-PAGE was visualized by the Coomassie-blue staining (FIG. 1A). Prior to staining with Coomassie Blue, images of fluorescent-SSA were obtained using blue light trans-illumination with an amber screen filter and captured using a GelDoc system (BioRad, CA) (FIG. 1B). In all cases images of fluorescent complexes were analysed in inverse form.

A replicate gel was transferred to nitrocellulose and probed with a 1:300 dilution of subject serum containing anti-SSA antibodies overnight at room temperature. The blot was blocked for 1 hour with buffer containing 1% bovine serum albumin, washed and then probed with alkaline phosphatase conjugated anti-human IgG for 1 hour. The blot was washed again and then developed using NBT/BCIP alkaline phosphate substrate (FIG. 1C).

As discussed previously, the attachment of a fluorophore to an autoantigen constitutes a covalent modification that could conceivably result in the modification of amino acids that are important for autoantigen epitopes and thereby reduce reactivity with subject autoantibodies. Accordingly, this example shows that fluorescent labelling under the conditions described does not result in a discernable change to the molecular weight of SSA antigen (assessed by SDS-PAGE).

Without wishing to be bound by any theory, the applicant believes that this result suggests that only a very limited number of amino acids are modified by the labelling process (FIG. 1A). As would be expected, these results clearly show that fluorescently labelled SSA antigen is readily detected using blue-light trans-illumination, whereas the unlabelled SSA antigen is not (FIG. 1B). Immunoblotting using a subject serum containing anti-SSA antibodies confirms that fluorescent labelling does not substantially alter or reduce the reactivity of SSA to subject autoantibodies (FIG. 1C).

Example 2

Determination of the Binding Characteristics of SMFLTA or SMFLTAA by ELISA

Enzyme-linked immunosorbent assay (ELISA) was performed according to Charles & Maini 1993 Man. Biol. Mark. Dis. (Kluwer Academic) using Nunc MaxiSorb plates and anti-IgG horse radish peroxidase conjugate. AlexaFluor 488-labelled and unlabelled SSA were coated onto ELISA plates (Nunc Thermo, Fisher, N.Y.) at 0.25, 0.5 and 1 µg/ml (100 µl per well) overnight at 4° C. Plates were washed and blocked for 4 hrs at room temperature prior to the addition of 7 serum samples diluted 1:100 (1 healthy donor and 6 subject serum samples containing anti-SSA antibodies) for 1 hour. ELISA plates were washed and incubated with horse radish-conjugated anti-human IgG at 1:30,000 dilution (Jackson Immunoresearch, PA) for 1 hour. Plates were washed and developed using TMB (3,3',5,5'-tetramethylbenzidine) substrate for 10 min and the reaction stopped using $H_2SO_4$ and the absorbance read at 450 nm.

ELISA was used to further evaluate the reactivity of fluorescently labelled SSA antigen relative to unlabelled SSA (FIG. 2). No discernable change in reactivity with subject autoantibodies was found when labelled and unlabelled SSA were coated onto ELISA plates at three different concentrations. This result suggests that attachment of the fluorophore to SSA antigen does not result in modification or reduction of target autoantigen access to target autoepitopes.

Example 3

Comparison of Autoantibody Detection Using DID and Fluorescence Detection of SMFLTAA in Precipitins as Compared to Epi-Illumination The utility of fluorescent labelled SSA to detect precipitating autoantibodies was investigated using DID. A patient serum containing anti-SSA antibodies was left undiluted or diluted 4-, 16-, 32-, 64- and 128-fold and then 5 µl were added to wells 1-6 respectively of four DID plates (FIG. 3). 5 µl of AlexaFluor 488-labelled SSA at a concentration of 6.25, 12.5, 25, and 50 µg/ml were added to the central well (FIG. 3). The DID plates were sealed, incubated at room temperature in the dark for 24 hours and AlexaFluor 488-SSA precipitin complexes were then detected using blue light trans-illumination with amber filter.

Immunoprecipitation complexes (i.e., white precipitin bands) were also evaluated by non-fluorescent detection (epi-illumination with white light against a black background) using a Molecular Dynamics Personal Densitometer SI and ImageQuant™ software (GE Healthcare).

Results are shown for undiluted or 4-, 16-, 32-, 64- and 128-fold diluted subject serum (wells 1-6 respectively) using 5 µl of 50 µg/ml AlexaFluor 488-labelled SSA in the central well (FIG. 4A—blue light trans-illumination with amber filter; FIG. 4B—white light epi-illumination against a black background).

The results of the DID assay show the differences in the reactivity of different amounts of labelled SSA antigen with different dilutions of a subject serum containing autoantibodies to SSA. A clear precipitin reaction was detectable with serum dilutions as high as 1:128.

The improved sensitivity of the DID procedure when using fluorescent labelled SSA followed by blue light trans-illumination is clearly shown in FIG. 4. Using small molecule fluorescence-labelled SSA, precipitin bands can be clearly seen at serum dilutions as high as 1:128. This is compared to the traditional method for detecting precipitin bands formed in DID assays using white light epi-illumination against a black background. In such traditional methods, precipitin bands were only detected from subject serum dilutions as low as 1:16.

Example 4

Semi-Quantitative Evaluation of Fluorescent DID

The precipitin bands formed by small molecule fluorescence-labelled SSA bound to its cognate antibody in subject sera were semi-quantitatively evaluated by scanning fluorescent DID images using the BioRad Quantity One (BioRad, CA) software (FIG. 5). Semi-quantitative evaluation by densitometric image-scanning was followed by pixel-counting of the precipitin band. Scans for subject sera that are 0, negative; 1, low-positive; 2, mid-positive; 3, high-positive for SSA autoantibodies are shown in FIG. 5.

Example 5

Detection of Anti-SSA Antibodies

Comparison of DID and ELISA Methods

The level of anti-SSA antibodies was measured in 48 serum samples (including two healthy donors) by direct ELISA, using unlabelled SSA for coating (1:100 dilution, each sample measured in duplicate) as described for FIG. 2, and by DID using AlexaFluor 488-labelled SSA. The DID plates were sealed, incubated at room temperature in the dark for 24 hrs and fluorescent precipitin bands were detected using blue light trans-illumination. The digital images obtained were quantified using Quantity One software (Bio-Rad, CA) and scored as described in Example 4. The DID score and ELISA absorbance were plotted to observe a good correlation ($r^2$=0.7107) between the two methods of SSA autoantibody measurement (FIG. 6).

A large number of subject sera were evaluated using this procedure and compared with results obtained using the ELISA procedure. The results show that there is generally a broad correlation between the two methods. In particular, detection of anti-SSA in sera giving higher ELISA results generally also gave the strongest precipitin bands analyzed after DID assay. However, the fluorescent DID method did not detect precipitating antibodies in some sera that gave lower ELISA results suggesting either (1) these sera were incorrectly assessed by ELISA to be positive for SSA antibodies, or (2) DID has lower sensitivity than ELISA for the detection of SSA antibodies.

Example 6

Detection of 6 Different Anti-ENA Antibodies Using Fluorescent DID

Undiluted serum samples (5 μl) were pipetted in the same outer well (1-6) of 6 DID plates (FIG. 7). The serum samples contained autoantibodies of the following specificities: well 1, anti-SSA and anti-SSB; well 2, healthy donor (no autoantibodies); well 3, anti-Jo-1; well 4, anti-RNP/Sm; well 5, anti-Sm; well 6, anti-Scl-70 (FIG. 7). AlexaFluor 488-labelled autoantigens (5 μl at 25 μg/ml) were added to the central well of the DID plates as follows: A, SSA; B, SSB; C, Jo-1; D, RNP/Sm; E, Sm, and F, Scl-70 (FIG. 7). The DID plates were sealed, incubated at room temperature in the dark for 24 hours and fluorescent precipitin bands were detected using blue light trans-illumination with amber filter.

The results show that SMFLTAAs according to the invention may be used to detect a range of autoantigens following the methods of the invention, while retaining their selectivity and sensitivity for their cognate autoantibodies. In particular, these results show that a range of SMFLTAAs (i.e., SSA, SSB, RNP/Sm, Sm, Jo-1 and Scl-70) according to the invention may be used in a DID assay to selectively and specifically detect their respective cognate autoantibodies in subject samples.

Example 7

Detection of 6 Different Anti-ENA Specificities Using Fluorescent CIE

Counter-immunoelectrophoresis (CIE) is considered to be more rapid and sensitive than DID for the detection of precipitating autoantibodies.

Counter-immunoelectrophoresis was performed using a 1.0% agarose gel with Tris-Tricine buffer (pH 8.6). 10 μl of undiluted serum samples (1 healthy donor and 3 containing auto-antibodies for each antigen tested) were added to wells at the anodal side of the gel and electrophoresed at 50V for 30 mins. (FIG. 8). AlexaFluor 488-labelled autoantigens (5 μl of 25 μg/ml) were then added to the cathodal wells, which were separated by 5 mm from the serum samples (FIG. 8). The gels were electrophoresed for a further 90 mins (120 mins for Jo-1) at 50V and fluorescent precipitin bands were detected using blue light trans-illumination. Results for one healthy donor (−ve) and three subject samples with autoantibodies specific for each autoantigen are shown.

The results from CIE detection of SMFLTAAs according to the invention show that the labelled autoantigens can be used to effectively detect subject autoantibodies specific for SSA, SSB, RNP/Sm, Sm, Jo-1 or Scl-70 using this procedure.

Example 8

Detection of Antibodies by Counterimmunoelectrophoresis (CIE)

Preparation of Agarose Gels for CIE

Heated liquid agarose was applied to the recessed area of a mold (A) and then GelBond (Lonza Rockland, Inc.) was layered on top (FIG. 10). Once the agarose had solidified it adhered to the GelBond after the GelBond was peeled away (B). Sample wells were formed by upstanding protrusions at the centre of the mold recess. Serum samples were applied to the larger anodal wells (3×4 mm, 1 mm deep) while AlexaFluor 488 labelled autoantigens were applied to the smaller cathodal wells (3×2 mm, 1 mm deep). Wells were separated by 5 mm.

Time Course, for Detection of Autoantibodies by CIE

Figure 11:
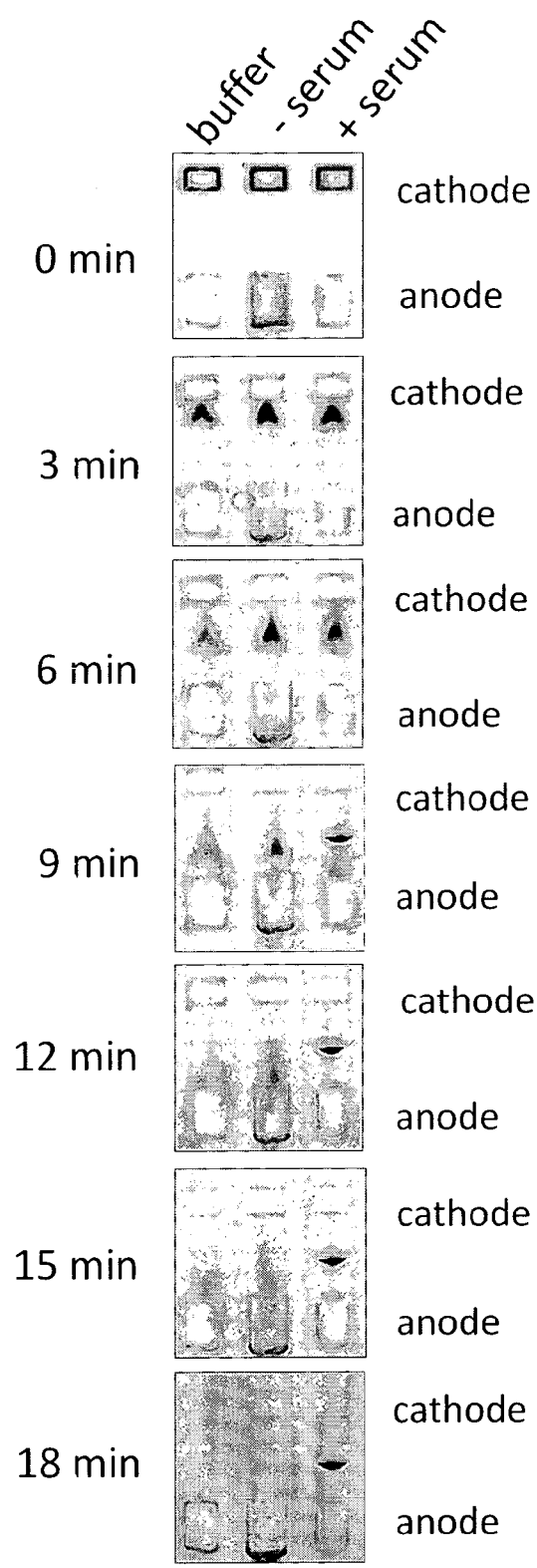

A negative control (buffer), a negative serum, and a patient serum containing anti-SSA autoantibodies were added to the anodal wells of a CIE gel (FIG. 11). AlexaFluor 488 labelled SSA antigen was then added to the cathodal well opposite each sample and electrophoresis was carried out at 3 mA constant current for up to 90 minutes. At different time intervals the gel was viewed using blue light trans-illumination with an amber filter. At 9-12 minutes a clear precipitin band can be seen with the positive sample containing SSA autoantibodies but not with the negative control or with the negative serum sample.

The results of this time course assay clearly show that the fluorescence detection of autoantibodies from serum samples using a CIE assay according to the invention is achieved in as few as 9 minutes. The time required to detect autoantibodies in a patient sample is therefore significantly reduced as compared to DID assays or certain other CIE protocols. Rapid detection of autoantibodies using this CIE format has numerous advantages for clinical settings, including the potential for use in real time detection and diagnosis of autoimmune disease i.e., patient samples may be taken and analyzed within a single clinical visit.

Detection of Autoantibodies at Different Serum Dilutions Using CIE

Figure 12:
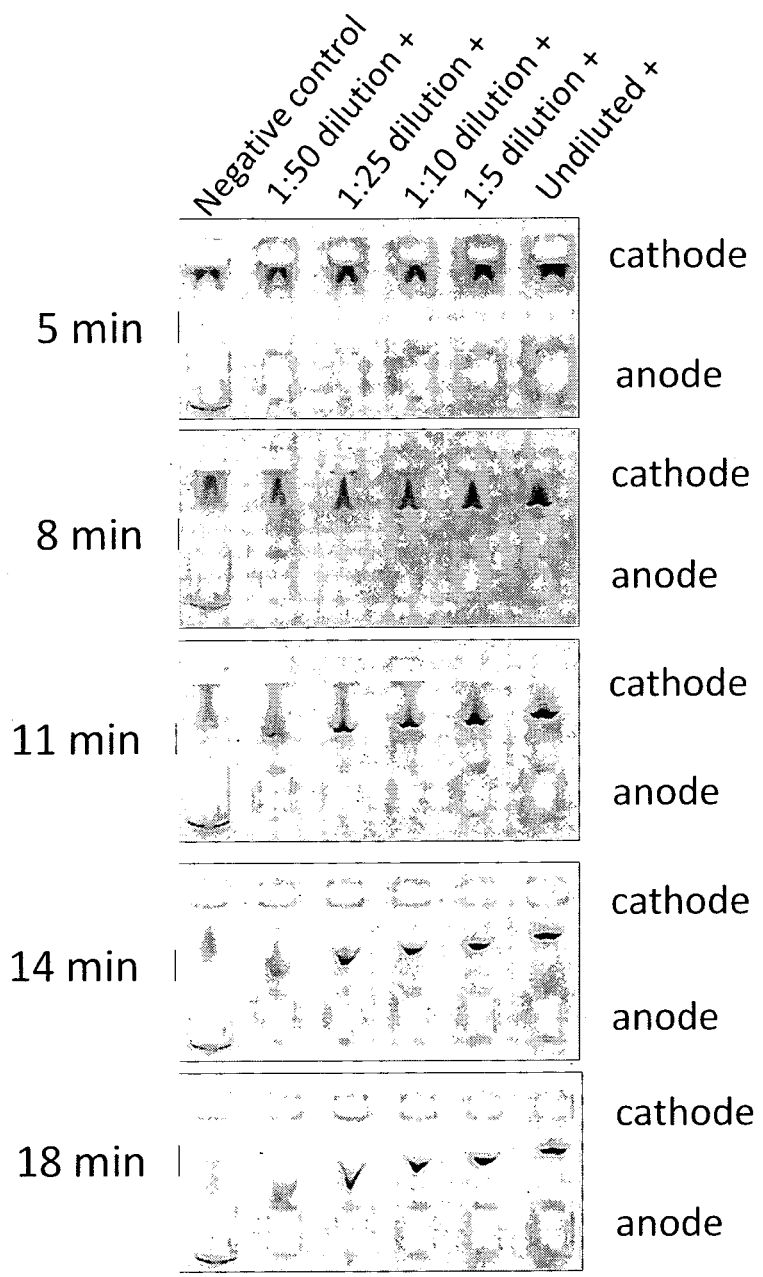

A negative control serum and a patient serum containing anti-SSA autoantibodies at different dilutions ranging from undiluted to 1:50 were added to the anodal wells of a CIE gel (FIG. 12). AlexaFluor 488 labelled SSA antigen was then added to the cathodal well opposite each sample and electrophoresis was carried out at 3 mA constant current. At different time intervals the gel was viewed using blue light trans-illumination with an amber filter. Clear precipitin bands can be seen with the positive sample containing SSA autoantibodies even when diluted 50-fold, but not with the negative control.

Detection of Autoantibodies Specific for Six Different Nuclear Antigens by Counterimmunoelectrophoresis (CIE)

Figure 13:
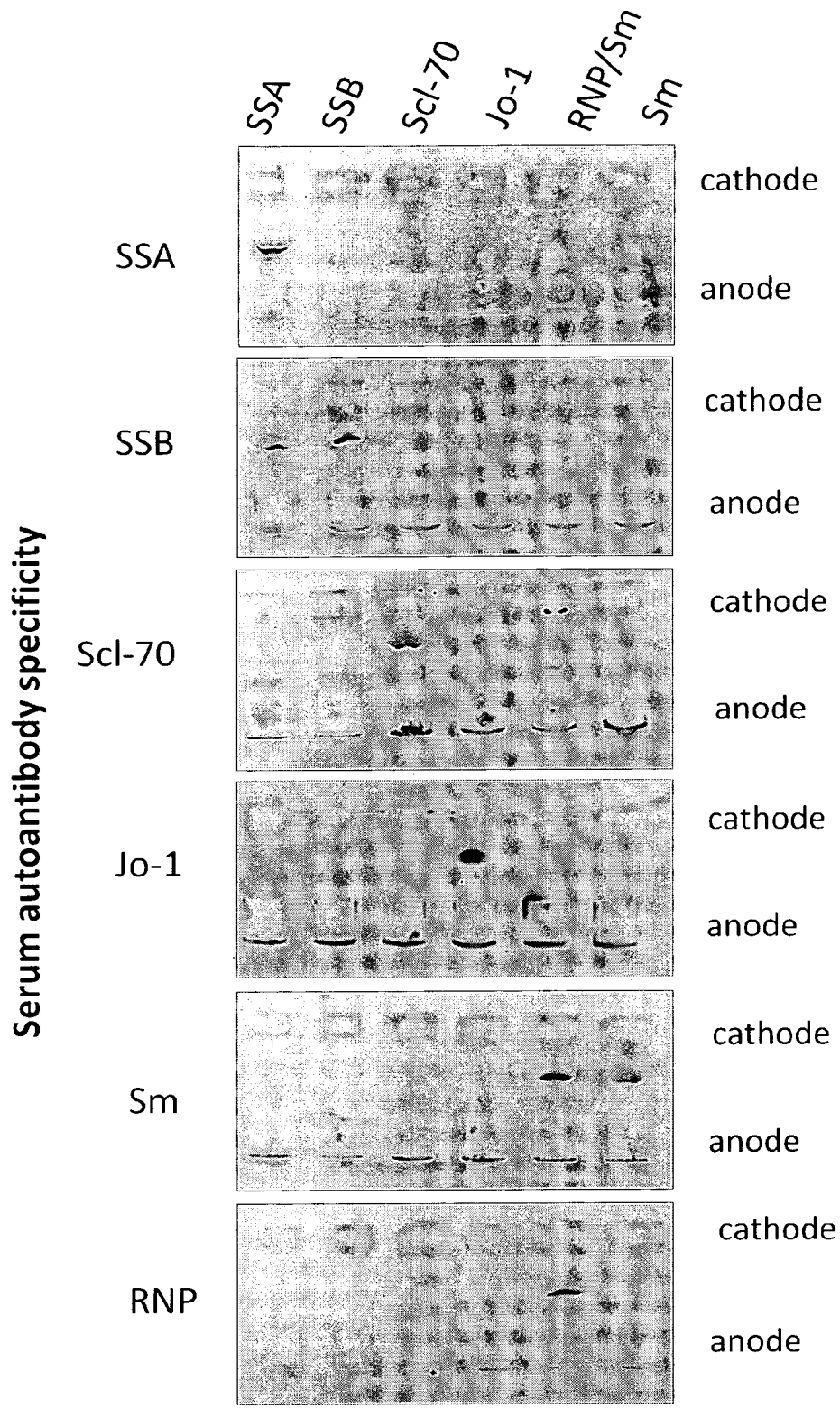

Patient sera containing autoantibodies with the following specificities (top to bottom-SSA, SSA/SB, Scl-70, Jo-1, Sm and RNP): were added to the anodal wells of a six different CIE gels (FIG. 13). AlexaFluor 488 labelled autoantigens (left to right) SSA, SSB, Scl-70, Jo-1, RNP/Sm, and Sm were then added to the cathodal wells of each gel. Electrophoresis was carried out at 3 mA constant current for 60 minutes. Using blue light trans-illumination with an amber filter, precipitin bands specific for each autoantibody specificity can be seen when the corresponding labelled autoantigen is applied to the opposing cathodal well.

Based on the above results showing the detection of six different autoantibodies specific for 6 different fluorescently labelled autoantigens, the skilled worker will recognize that the immunodetection methods according to the invention, particularly DID or CIE, may be employed with a wide range of different labelled antigens (and autoantigens) to detect their cognate antibodies.

The above examples illustrate practice of the invention. It will be appreciated by those skilled in the art that numerous variations and modifications may be made without departing from the spirit and scope of the invention.

References cited within this application, including patents, published applications and other publications, are hereby incorporated by reference.

The practice of the present invention will employ, unless otherwise indicated, conventional techniques of molecular biology and the like, which are within the skill of the art. Such techniques are explained fully in the literature. See e.g., *Molecular Cloning: A Laboratory Manual*, (J. Sambrook et al., Cold Spring Harbor Laboratory, Cold Spring Harbor, N.Y., 1989); *Current Protocols in Molecular Biology* (F. Ausubel et al., eds., 1987 updated); *Essential Molecular Biology* (T. Brown ed., IRL Press 1991); *Gene Expression Technology* (Goeddel ed., Academic Press 1991); *Methods for Cloning and Analysis of Eukaryotic Genes* (A. Bothwell et al. eds., Bartlett Publ. 1990); *Gene Transfer and Expression* (M. Kriegler, Stockton Press 1990); *Recombinant DNA Methodology II* (R. Wu et al. eds., Academic Press 1995); *PCR: A Practical Approach* (M. McPherson et al., IRL Press at Oxford University Press 1991); *Oligonucleotide Synthesis* (M. Gait ed., 1984); *Cell Culture for Biochemists* (R. Adams ed., Elsevier Science Publishers 1990); *Gene Transfer Vectors for Mammalian Cells* (J. Miller & M. Calos eds., 1987); *Mammalian Cell Biotechnology* (M. Butler ed., 1991); *Animal Cell Culture* (J. Pollard et al. eds., Humana Press 1990); *Culture of Animal Cells*, $2^{nd}$ Ed. (R. Freshney et al. eds., Alan R. Liss 1987); *Flow Cytometry and Sorting* (M. Melamed et al. eds., Wiley-Liss 1990); the series *Methods in Enzymology* (Academic Press, Inc.); Wirth M. and Hauser H. (1993); *Immunochemistry in Practice*, 3rd edition, A. Johnstone & R. Thorpe, Blackwell Science, Cambridge, Mass., 1996; *Techniques in Immunocytochemistry*, (G. Bullock & P. Petrusz eds., Academic Press 1982, 1983, 1985, 1989); Handbook of Experimental Immunology, (D. Weir & C. Blackwell, eds.); *Current Protocols in Immunology* (J. Coligan et al: eds. 1991); *Immunoassay* (E. P. Diamandis & T. K. Christopoulos, eds., Academic. Press, Inc., 1996); Goding (1986) *Monoclonal Antibodies: Principles and Practice* (2d ed) Academic Press, New York; Ed Harlow and David Lane, *Antibodies A laboratory Manual*, Cold Spring Harbor Laboratory, Cold Spring Harbor, N.Y., 1988; *Antibody Engineering*, $2^{nd}$ edition (C. Borrebaeck, ed., Oxford University Press, 1995); and the series Annual Review of Immunology; the series Advances in Immunology.

The skilled person will appreciate that the invention as set forth and described herein is not limited solely to the aspects, embodiments, and examples as described, but also encompasses within the spirit and scope of the invention, those variations and modifications of the invention as would be obvious to the person of skill in the art (including the person of ordinary skill in the art) in view of the disclosures provided herein and the common general knowledge.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

ADDITIONAL REFERENCES

All additional references and citations in this list are also hereby incorporated in their entirety.

Laemmli U K 1970 *Nature* 227: pp. 680-685

Towbin et al. 1979 *Proc. Natl. Acad. Sci. USA* 76: pp. 4350-4354

Charles P J & Maini R N 1993 *Man. Biol. Mark. Dis. A*5:1-23 (Kluwer Academic)

Bowie et al., 1990, *Science* 247, 1306

Bunn C & Kveder T 1993 *Man. Biol. Mark. Dis. A*3:1-12 (Kluwer Academic)

Deutscher 1990, Ed, Methods in Enzymology, Vol. 182, *Guide to Protein Purification*.

Kavanaugh et al. 2000 *Arch. Pathol. Lab. Med.* 124: pp: 71-81

What is claimed is:

1. A method of detecting a target autoantibody in a sample, comprising the steps of:
   a. contacting the sample with a small molecule fluorophore-labelled target protein autoantigen that specifically binds to the target autoantibody, wherein the contacting comprises diffusion of the target autoantibody and the small molecule fluorophore-labelled target protein autoantigen through a gel to reach equivalent concentrations at a particular location in the gel to form an immunoprecipitate of the target autoantibody and the small molecule fluorophore-labelled target protein autoantigen; and
   b. detecting the presence of the target autoantibody bound to the small molecule fluorophore-labelled target protein autoantigen,
   wherein the small molecule fluorophore-labelled target protein autoantigen comprises a nuclear autoantigen selected from the group consisting of Jo-1 antigen, Ro60 SSA antigen, La SSB antigen, Sm antigen, Sm/RNP complex antigen, and Scl-70 antigen.

2. The method according to claim 1, wherein the detecting step b) is fluorescence detection of the small molecule fluorophore-labelled target protein autoantigen in the immunoprecipitate.

3. The method according to claim 1, wherein the sample is a clinical sample obtained from a subject having or suspected of having a particular autoimmune disorder, wherein the method is performed concurrently with a control sample, the control sample either lacking target autoantibodies or containing known concentrations of control autoantibodies.

4. The method according to claim 2, wherein the target autoantibody is detected in a blood, plasma or serum sample obtained from a subject at a dilution of from about 1:1 to about 1:256 (sample:diluent).

5. The method according to claim 1, wherein the contacting step a) is carried out by double immunodiffusion (DID) assay or counter-immunoelectrophoresis (CIE) assay,
   wherein the contacting step a) is performed using an immunoprecipitation device selected from the group consisting of an immunodiffusion device, a micro-immunodiffusion device, a counterimmunoelectrophoresis (CIE) device and a micro-counterimmunoelectrophoresis device; and
   wherein the detecting step b) is fluorescence detection of the small molecule fluorophore-labelled target protein autoantigen in the immunoprecipitate.

6. A method of detecting a target autoantibody in a sample, comprising the steps of:
   a. contacting the sample with a target protein autoantigen that has been chemically labelled with a small molecule fluorophore, wherein the labelled target protein autoantigen specifically binds to the target autoantibody, wherein the contacting comprises:
   diffusion of the target autoantibody and the small molecule fluorophore-labelled target protein autoantigen through a gel to reach equivalent concentrations at a particular location in the gel to form an immunoprecipitate of the target autoantibody and the small molecule fluorophore-labelled target protein autoantigen, wherein the diffusion is performed using an immunoprecipitation device selected from the group consisting of an immunodiffusion device, a micro-immunodiffusion device, a counterimmunoelectrophoresis (CIE) device and a micro-counterimmunoelectrophoresis device; and b. detecting the presence of the target autoantibody bound to the labelled target protein autoantigen in an immunoprecipitate, wherein the labelled protein target autoantigen comprises a nuclear autoantigen selected from the group consisting of Jo-1 antigen, Ro60 SSA antigen, La SSB antigen, Sm antigen, Sm/RNP complex antigen, and Scl-70 antigen.

7. The method according to claim 6, wherein the detecting step b) is fluorescence detection of the small molecule fluorophore-labelled target protein autoantigen in the immunoprecipitate.

8. The method according to claim 6, wherein the sample is a clinical sample obtained from a subject having or suspected of having a particular autoimmune disorder, wherein the method is performed concurrently with a control sample, the control sample either lacking target autoantibodies or containing known concentrations of control autoantibodies.

9. The method according to claim 7, wherein the target autoantibody is detected in a blood, plasma or serum sample obtained from a subject at a dilution of from about 1:1 to about 1:256 (sample:diluent).

* * * * *